United States Patent
Theofilos

(10) Patent No.: US 11,944,357 B2
(45) Date of Patent: Apr. 2, 2024

(54) MINIMALLY INVASIVE SURGERY ADD ON SCREW SYSTEM

(71) Applicant: SNJ Patents, LLC, Palm Beach Gardens, FL (US)

(72) Inventor: Charles Theofilos, Palm Beach Gardens, FL (US)

(73) Assignee: SNJ Patents, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/891,762

(22) Filed: Aug. 19, 2022

(65) Prior Publication Data

US 2023/0055375 A1 Feb. 23, 2023

Related U.S. Application Data

(60) Provisional application No. 63/235,470, filed on Aug. 20, 2021.

(51) Int. Cl.
*A61B 17/70* (2006.01)
*A61B 17/02* (2006.01)

(52) U.S. Cl.
CPC ........ *A61B 17/708* (2013.01); *A61B 17/0218* (2013.01); *A61B 17/7032* (2013.01); *A61B 17/7037* (2013.01)

(58) Field of Classification Search
CPC .. A61B 17/7043; A61B 17/7049–7052; A61B 17/7056; A61B 17/7058
See application file for complete search history.

(56) References Cited

U.S. PATENT DOCUMENTS

| | | | |
|---|---|---|---|
| 2004/0158247 A1* | 8/2004 | Sitiso | A61B 17/7091 606/907 |
| 2010/0160981 A1* | 6/2010 | Butler | A61B 17/7049 606/308 |
| 2011/0106178 A1* | 5/2011 | Schwab | A61B 17/7037 606/305 |
| 2012/0031792 A1* | 2/2012 | Petit | A61B 50/30 606/86 A |
| 2015/0032158 A1* | 1/2015 | Khajavi | A61B 50/30 606/246 |
| 2016/0030087 A1* | 2/2016 | Mclean | A61B 17/7011 606/260 |
| 2017/0290611 A1* | 10/2017 | Bootwala | A61B 17/7049 |
| 2017/0348024 A1* | 12/2017 | Abell | A61B 17/7089 |
| 2021/0045785 A1* | 2/2021 | Haziza | A61B 17/7008 |
| 2022/0061891 A1* | 3/2022 | Lengyel | A61B 17/7032 |
| 2022/0354542 A1* | 11/2022 | Ebara | A61B 17/7032 |

FOREIGN PATENT DOCUMENTS

WO   WO-2008140756 A2 * 11/2008   ......... A61B 17/7052

* cited by examiner

*Primary Examiner* — Eduardo C Robert
*Assistant Examiner* — Michelle C Eckman
(74) *Attorney, Agent, or Firm* — McHale & Slavin, P.A.

(57) ABSTRACT

A system, medical devices, and methods for use in surgical procedures, such as spinal surgeries. The system, medical devices, and methods are designed to provide a surgeon the ability to add a screw connector, or screw head such as a tulip, to pre-existing implanted bone, such as pedicle, facet, lateral mass, etc., screw system without having to remove the previously implanted screws and/or rods already existing in a patient.

8 Claims, 40 Drawing Sheets

MINIMALLY INVASIVE SURGERY ADD ON SCREW SYSTEM

CROSS-REFERENCE TO RELATED APPLICATIONS

This application claims priority to U.S. Provisional Application No. 63/235,470, filed on Aug. 20, 2021, entitled "MINIMALLY INVASIVE SURGERY ADD ON SCREW SYSTEM," which is hereby incorporated herein by reference in its entirety as an example.

FIELD OF THE INVENTION

The present invention relates to medical devices, systems, and methods; to medical devices, systems, and methods used in minimally invasive surgical procedures; to medical devices, systems, and methods related to spinal surgeries; to medical devices, systems, and methods for adding additional surgical devices, such as a retractor or pedicle screw, or other bone screws, to existing surgical hardware, i.e., pedicle screws or rods already existing in a patient.

BACKGROUND OF THE INVENTION

Pedicle screw systems, such as those described in U.S. Pat. No. 9,456,859, U.S. Patent Application Publication No. 2014/0336709, and U.S. Patent Application Publication No. 2007/0239159 are typically utilized in spinal surgery to fixate the spine, including fusion surgeries from the occipital, cervical, thoracic, lumbar, sacral/coccyx spine, and pelvis. While these systems have been used for many years and are generally considered safe, such systems have their drawbacks and do not always result in a curing treatment for patients that have undergone such surgical procedures.

In the case of spinal fusion procedures, statistically, roughly three percent (3%) of patients who have undergone such a surgical procedure each year require additional surgery. Such patients typically require secondary surgical procedures to adjacent levels, this due to the additional stress added by the fusion levels. When there are existing bone screws in the spine and a level above and/or below have to be added, unfortunately, there is already a screw and rod in one of the vertebrae that will be part of the fusion during the secondary surgery performed. Utilizing minimally invasive techniques require that both vertebrae being fused have no screws in them so the surgeon can add screws attached to retractor blades, and then attach an external retractor device, if needed, to these retractor blades. This allows the surgeon to have exposure to the surgical level, as well as to perform distraction across the disc level, allowing the surgeon to insert the appropriate size cage in the disc space if needed. When a vertebra (vertebrae) already has a screw in it attached to a rod from a previous fusion, the surgeon is forced to either add a side connector to the rod, cut the rod and then remove the bone screw, or remove all the screws and rods from the previous fusion. Any one of such actions dramatically lengthens the time of the surgery, increases the infection risks, and increases the bleeding during surgical procedure. The present invention addresses these issues and provides a system, devices, and methods which can be used by the surgeon to avoid such problems.

Applicant's system, devices, and methods provide surgeons a mechanism to attach a retractor blade to an existing screw head. When completed with the surgical exposure fusion, surgeons are able to add a screw connector, or screw head such as a tulip, polyaxial, or monoaxial screw head, to the pre-existing implanted bone, such as pedicle, facet, lateral mass, etc., screw system without having to remove the previously implanted screws and/or rods. This dramatically decreases surgical time, as well as the risks and surgical exposure size for the patient. The patient should have less blood loss, less risk for infection, and a much quicker recovery with less postoperative pain.

SUMMARY OF THE INVENTION

The present invention relates to a system, medical devices, and methods for use in surgical procedures, such as spinal surgeries. The system, medical devices, and methods are designed to provide a user the ability to add a screw connector, or screw head such as a tulip, to the pre-existing implanted bone, such as pedicle, facet, lateral mass, etc., screw system without having to remove the previous implanted screws and/or rods already existing in a patient.

Accordingly, it is an objective of the invention to provide a system for use in surgical procedures.

It is a further objective of the invention to provide medical devices for use in surgical procedures.

It is a further objective of the invention to provide medical devices for use in surgical procedures in which a surgeon is required to add surgical devices, such as a screw connector, or screw head such as a tulip, to a pre-existing implanted bone screw system, such as pedicle, facet, lateral mass, etc., without having to remove the previous surgical devices, i.e. implanted screws and/or rods, already existing in a patient.

It is yet another objective of the invention to provide methods for use in surgical procedures.

It is a further objective of the invention to provide methods for use in surgical procedures in which a surgeon is required to add surgical devices, such as a screw connector, or screw head such as a tulip, to a pre-existing implanted bone screw system, such as pedicle, facet, lateral mass, etc., without having to remove the previous surgical devices, i.e. implanted screws and/or rods, already existing in a patient.

It is a still further objective of the invention to provide a system for use in spinal procedures.

It is a further objective of the invention to provide medical devices for use in spinal procedures.

It is yet another objective of the invention to provide methods for use in spinal procedures.

It is a still further objective of the invention to provide a system configured to allow a user the ability to add surgical devices, such as a screw connector, or screw head such as a tulip, to pre-existing implanted bone, such as pedicle, facet, lateral mass, etc., screw system without having to remove the previous surgical devices, i.e. implanted screws and/or rods, already existing in a patient.

It is a further objective of the invention to provide medical devices configured to allow a user the ability to add surgical devices, such as a screw connector, or screw head such as a tulip, to pre-existing implanted bone, such as pedicle, facet, lateral mass, etc., screw system without having to remove the previous surgical devices, i.e. implanted screws and/or rods, already existing in a patient.

It is yet another objective of the invention to provide methods which allow a user the ability to add surgical devices, such as a screw connector, or screw head such as a tulip, to pre-existing implanted bone, such as pedicle, facet, lateral mass, etc., screw system without having to remove the previous surgical devices, i.e. implanted screws and/or rods, already existing in a patient.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE INVENTION

Figure 1:
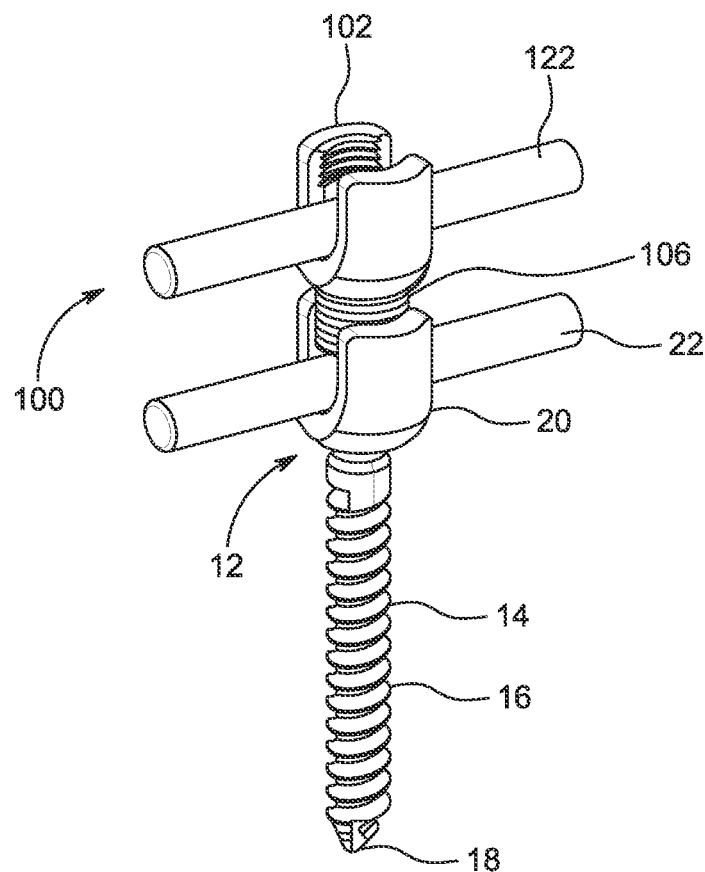
FIG. 1 illustrates a perspective view of an embodiment of an add-on screw system, illustrating a tulip within a tulip mechanism for securing an add on tulip to a preexisting tulip previously implanted into a patient.
Figure 2:
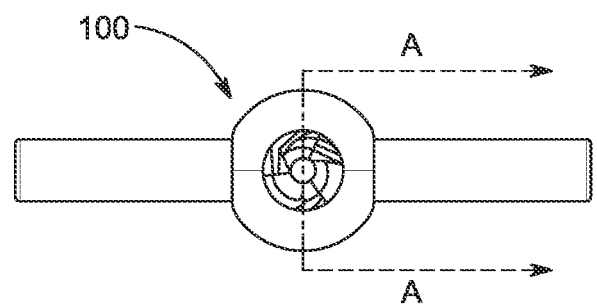
FIG. 2 is a top view of the add-on screw system illustrated in FIG. 1.
Figure 3:
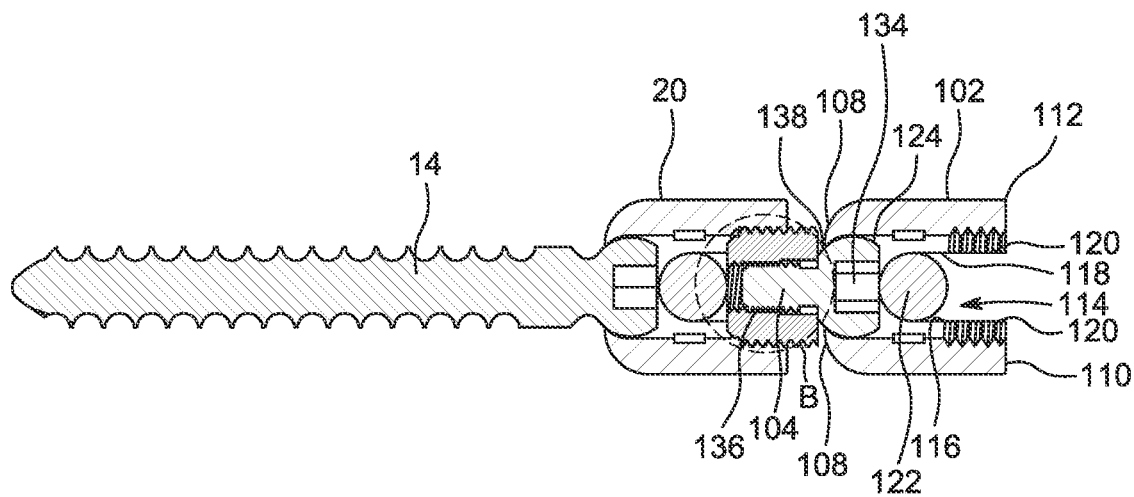
FIG. 3 is a cross section of the add-on screw system illustrated in FIG. 1, taken along lines A-A in FIG. 2.
Figure 4:
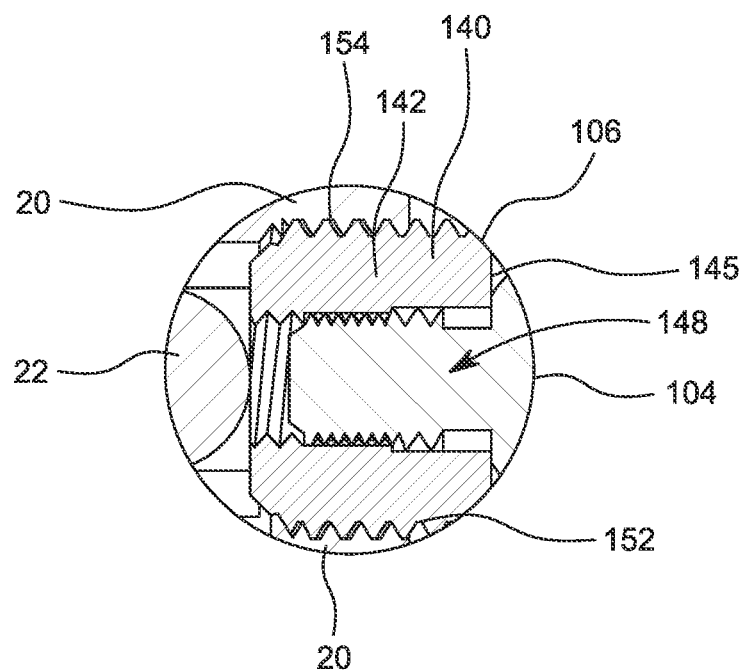
FIG. 4 is an enlarged view of Section B shown in FIG. 3.
Figure 5:
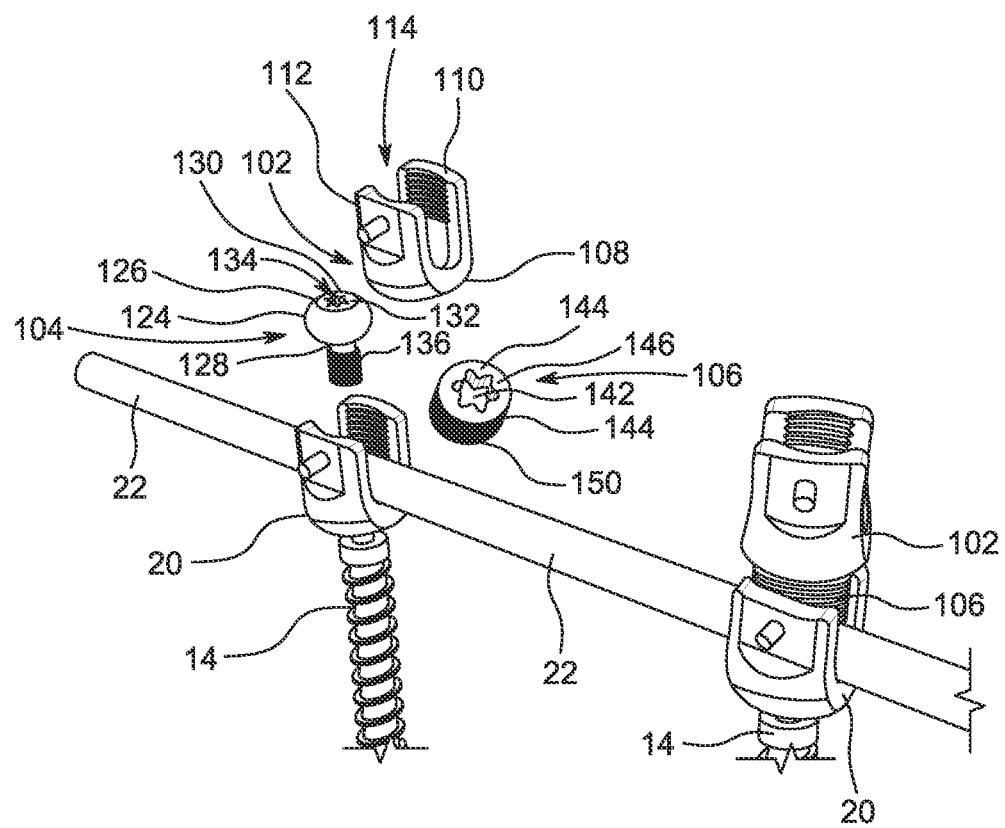
FIG. 5 is an exploded view of the add-on screw system illustrated in FIG. 1.
Figure 6:
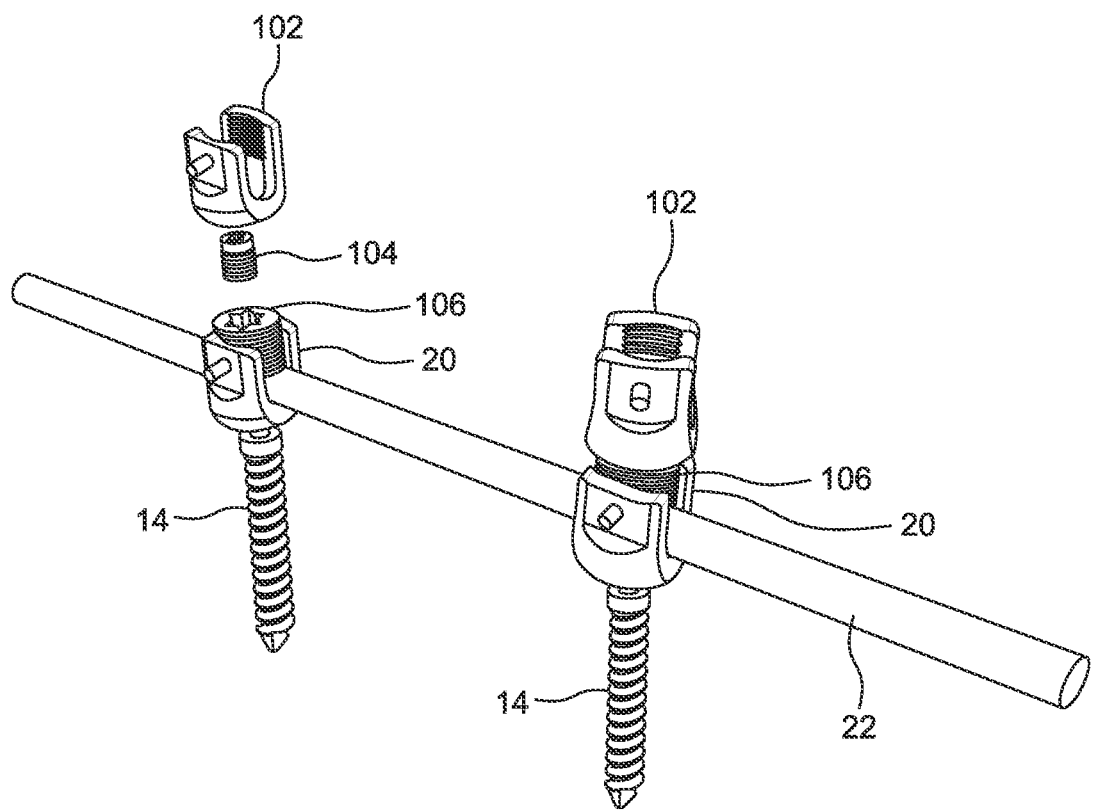
FIG. 6 illustrate add-on screw system units secured to a surgical rod.
Figure 7:
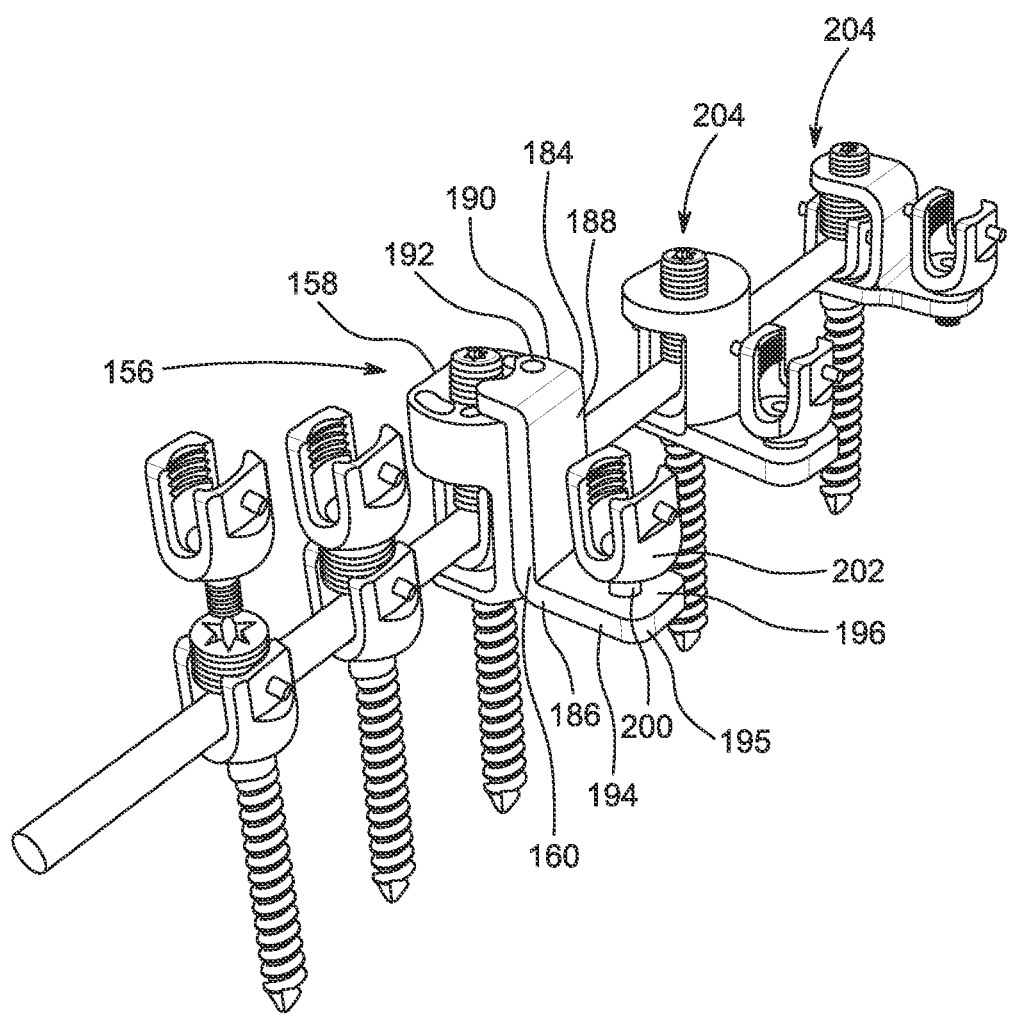
FIG. 7 illustrates a perspective view of an embodiment of an add-on screw system, utilizing a tulip to side tulip mechanism for securing the add on tulip to a preexisting tulip previously implanted into a patient.
Figure 8:
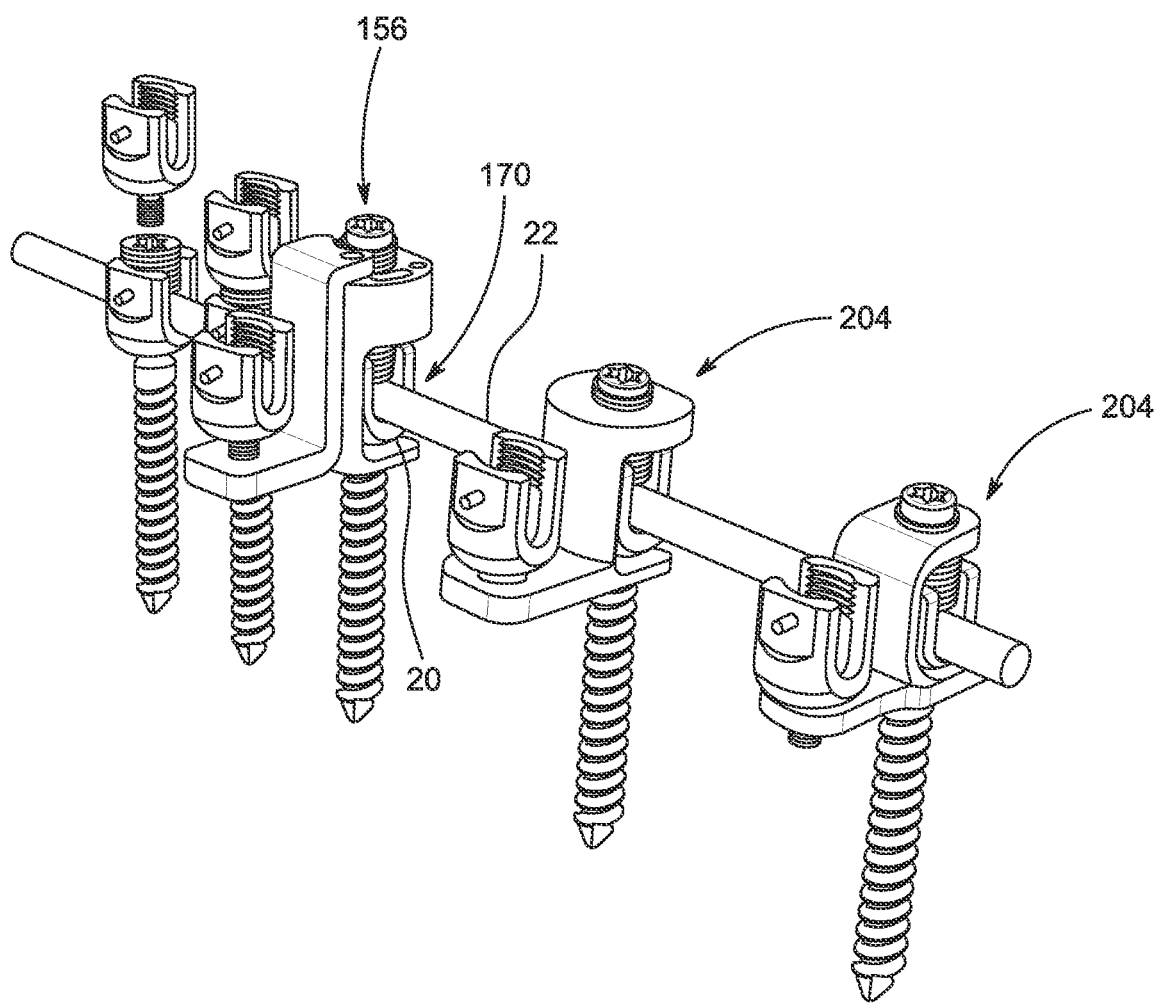
FIG. 8 is an alternative view of the add-on screw system illustrated in FIG. 7.
Figure 9:
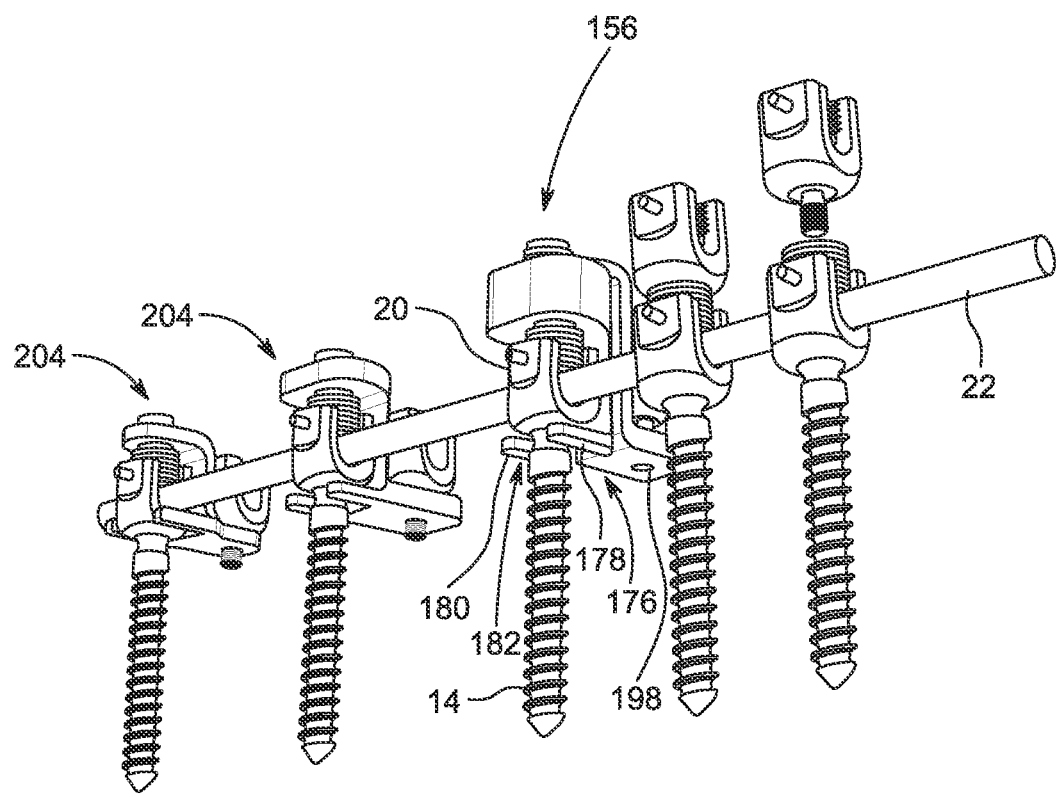
FIG. 9 is an alternative view of the add-on screw system illustrated in FIG. 7.
Figure 10:
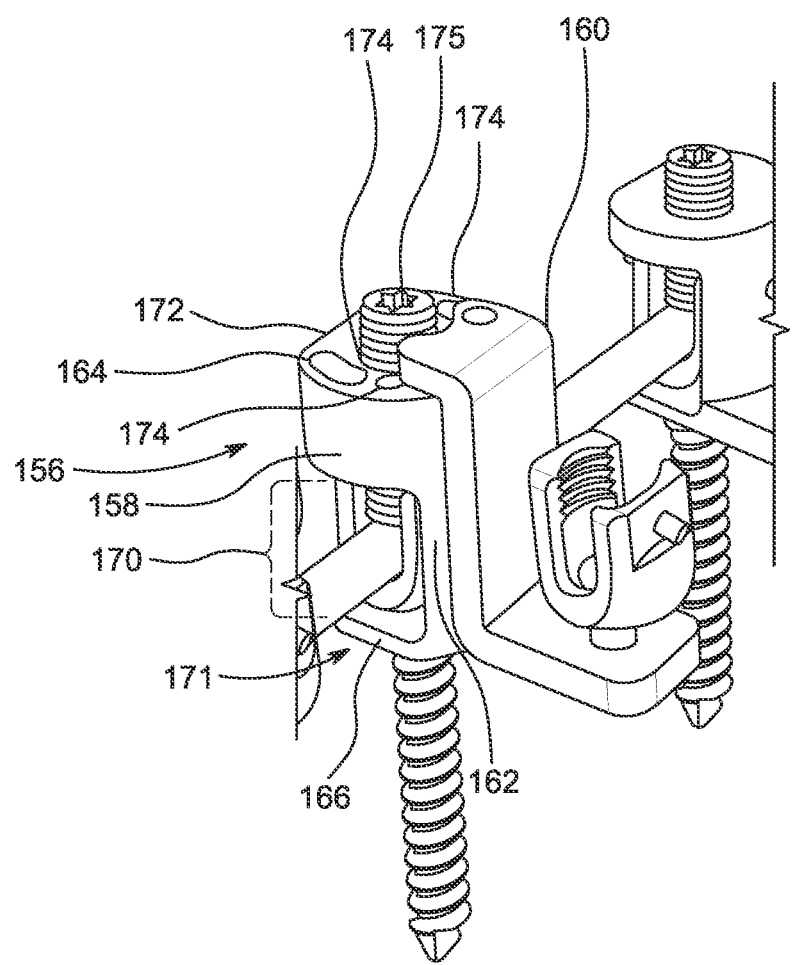
FIG. 10 is a perspective view of an embodiment of a two-component tulip to side tulip device.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-6, one or more components of an illustrative example of a surgical system for adding additional surgical devices to pre-existing surgical devices already in a patient, referred to generally as an add on screw system 100, is shown. While the add on screw system 100 is described for use with a pedicle (or bone, facet, lateral mass, etc.) screw related to spinal fusion procedures, the add on screw system 100 can be used in any orthopedic or spinal surgery in which a surgeon is required to add surgical devices, such as a screw connector, or screw head such as a tulip, to a pre-existing implanted bone screw system, such as pedicle, facet, lateral mass, etc., without having to remove the previous surgical devices, i.e. implanted screws and/or rods, already existing in a patient.

The add on screw system 100 is illustrated herein attached to a primary pedicle screw system 12, representing pre-existing surgical devices already existing in a patient. While described for use with a pedicle screw, add on screw system 100 may be used with other bone screws, facet screws, lateral mass screws, etc. The primary pedicle screw system 12, also referred to as the pre-existing pedicle system 12, comprises a pedicle screw 14 having a threaded body 16 and pointed distal end or tip 18. A pedicle screw head or tulip 20 secures to the pedicle screw threaded body 16 and is configured to receive a surgical rod 22 when inserted and held therein. The add on screw system 100 comprises a secondary tulip 102, referred to herein as the add on screw system tulip 102, an add on screw system head screw 104, and an add on screw system center threaded set screw 106.

The add on screw system tulip 102 is configured to receive and hold therein the screw system head screw 104, and includes a base, or seat, 108 separating side walls 110 and 112, and an interior 114. The interior 114 is defined by the space separating side walls 110 and 112. The inner surface 116 of side wall 110 and the inner surface 118 of side wall 112 may comprise internal threading 120 for engaging a set screw, thereby locking a secondary rod, or add on screw system rod, 122 in place between the side walls 110 and 112.

The add on screw system head screw 104 is configured to secure to the add on screw system center threaded set screw 106 at one end and to the add on screw system tulip 102 at another end. The add on screw system head screw 104 is shown having a main body 124, shown having a spherical shape, separating a first end 126 and a second end 128. The spherical shape provides for polyaxial movement or arrangement of the add on screw system tulip 102. The first end 126 has an upper surface 130 and an opening 132 exposing an interior 134. The opening 132 is sized and shaped to receive a head screw tightening device, such as a screwdriver or hex wrench. The opening 132 is shown assuming a hexagonal shape, but such shape is illustrative only.

Integrally formed from or attached to and extending from the screw system head screw main body 124 is an add on screw system center threaded set screw engagement member 136, illustrated herein as a generally cylindrically shaped threaded body. The screw system center threaded set screw engagement member threaded body 136 is sized and shaped to engage with, i.e., to secure into, a portion of the screw system center threaded set screw 106. In use, the add on screw system head screw 104 is placed within opening 138 of the add on screw system tulip 102 so a portion of the add on screw system head screw main body 124 rests on the add on screw system tulip seat 108. In this orientation, the screw system center threaded set screw engagement member threaded body 136 aligns with and engages with the add on screw system center threaded set screw 106.

The add on screw system center threaded set screw 106 is configured to secure the add on screw system tulip 102 to the pre-existing pedicle screw head or tulip 20. The add on screw system center threaded set screw 106 comprises a main body 140 having a thread on center 142. The add on screw system center threaded set screw main body 140 comprises an upper surface 145 having an opening 146, exposing an interior 148. The opening 146 is sized and shaped to receive a set screw tightening device, such as a screwdriver or hex wrench. The opening 146 is shown assuming a hexagonal shape, but such shape is illustrative only. The external surface 150 comprises threading 152 which is sized and shaped to engage with corresponding internal threading 154 of the pre-existing pedicle screw head or tulip 20. In use, the add on screw system center threaded set screw 106 is secured to the pre-existing pedicle screw head or tulip 20 by tightening the add on screw system center threaded set screw main body 140 via insertion of a set screw tightening device into the opening 146. Once secured, the add on screw system center threaded set screw engagement member threaded body 136 may be inserted into the interior 148 of the add on screw system center threaded set screw main body 140, engaging with the thread on center 142.

FIGS. 1-6 illustrate the add on screw system 100 utilizing a tulip within a tulip mechanism for securing a new tulip to an existing tulip. FIGS. 7-12 illustrate the add on screw system 100 which utilizes a side-to-side tulip connecting mechanism. In one embodiment of the side-to-side tulip connecting mechanism, a two-component device, referred to herein as a two-component side tulip connector 156 is shown. The two-component side tulip connector 156 comprises a first component 158 configured to engage with and/or secure to a preexisting portion of a pedicle screw, preferably at or along the tulip portion, and a second component 160, configured to engage with at least a portion of the two-component side tulip connector first component 156 and a secondary tulip. The two-component side tulip connector first component 158 comprises a main body 162, an upper portion 164, and a lower portion 166. The two-component side tulip connector first component main body upper portion 164 is separated from the two-component side tulip connector first component main body lower portion 166 by a space 170, forming a receiving channel 171.

The receiving channel 171 is sized and shaped to receive and store therein the pre-existing tulip head 20 and/or rod 22. The upper surface 172 of the two-component side tulip connector first component main body upper portion 164 may comprise one or more openings 174 sized and shaped to receive different structures, such as a set screw 175, for securing the two-component side tulip connector 156 to the pre-existing tulip head 20, for securing the two-piece side tulip connector second component 160 to the two-piece side tulip connector first component 158, or for securing to a retractor blade thereto.

The two-piece side tulip connector first component lower portion 166 comprises a preexisting pedicle screw engagement member 176. The preexisting pedicle screw engagement member 176 is illustrated having two arms or finger-like projections 178 and 180 extending away from the two-piece side tulip connector first component 158 main body 162. The arms or finger-like projections 178 and 180 are separated by a space 182 sufficient in size to accommodate at least a portion of a preexisting pedicle screw threaded body 16 to rest or be placed therein. As shown, the arms or finger-like projections 178 and 180 are placed at or near where the preexisting pedicle screw threaded body 16 exits from the preexisting tulip 20 and resting under the preexisting tulip 20.

The two-piece side tulip connector second component 160 comprises a first end 184, a second end 186, and a main body 188 separating the first end 184 and the second end 186. The two-piece side tulip connector second component first end 184 is designed to engage with at least a portion of the two-piece side tulip connector 156 and may contain an upper platform section 190 which may extend away from the main body 188, forming a curved or angled section. The upper platform section 190 may have an opening 192 which may be placed over opening 174. Insertion of a screw therein provides a mechanism to lock the second component 160 to the first component 158. The second end 186 may contain a secondary tulip engaging member 194, illustrated herein as a lower platform 195 with a surface 196 extending away from the main body 188. An opening 198 rests within the surface 196 and is sized and shaped to receive a tulip securing screw 200. The lower platform 194 positions the secondary tulip 202 next to and in a side-by-side relationship. In this position, a secondary rod may be attached to the preexisting tulip 20.

Figure 11A:
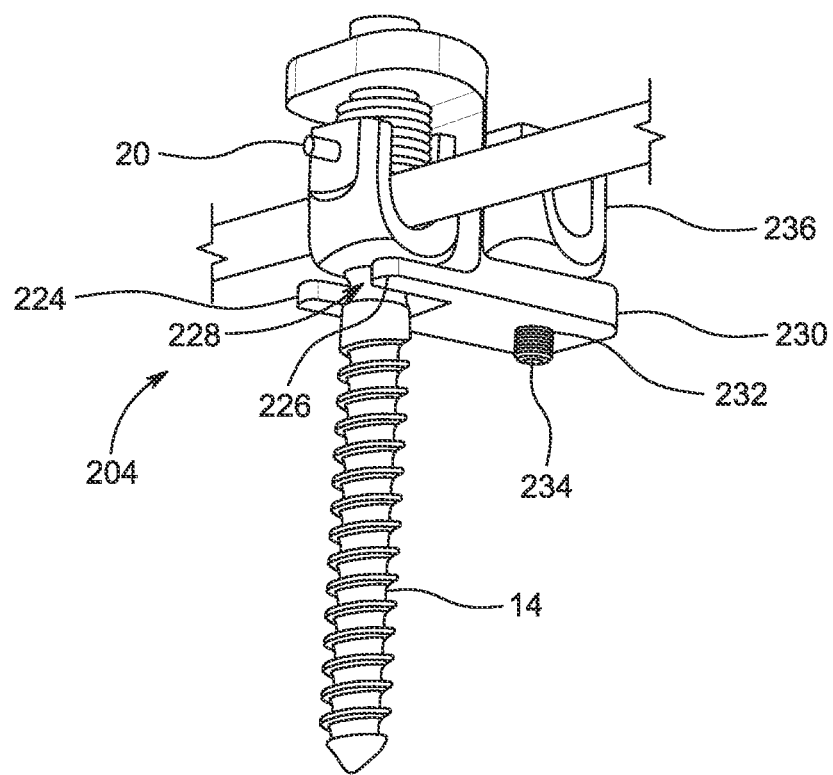
FIG. 11A is a perspective view of an embodiment of a one-component tulip to side tulip device.
Figure 11B:
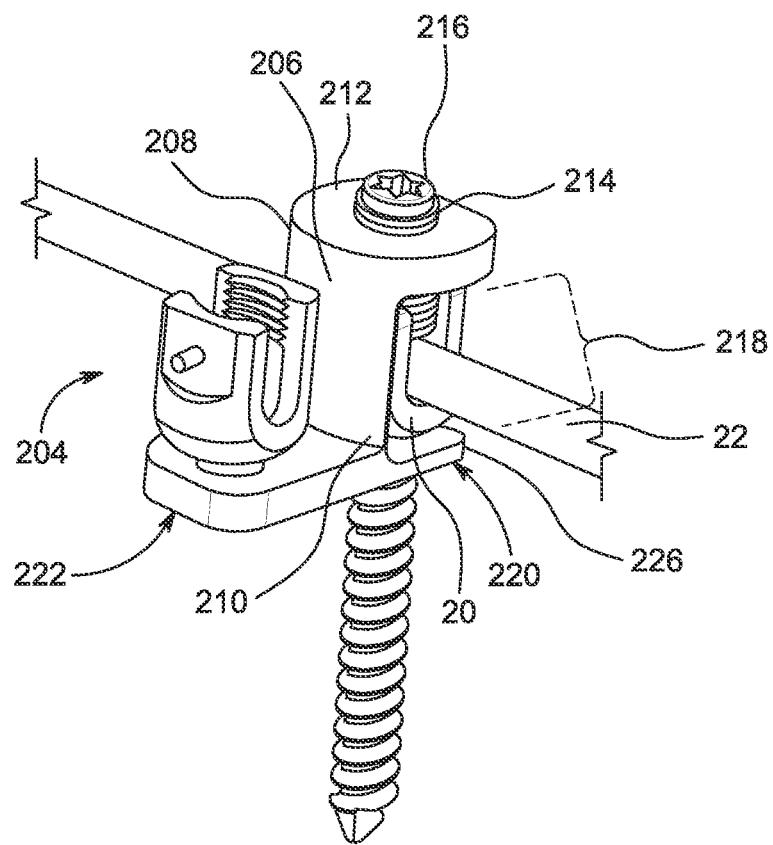
FIG. 11B is an alternative perspective view of the one-component tulip to side tulip device.

Referring to FIGS. 11A and 11B, an embodiment of the side-to-side tulip connecting mechanism illustrated as a one-component device, referred to herein as a one-piece side tulip connector 204, is shown. The one-piece side tulip connector 204 is configured to engage with and/or secure to a preexisting portion of a pedicle screw and with a secondary tulip. The one-piece side tulip connector 204 comprises a main body 206 having an upper end 208 and a bottom end 210. The upper end 208 comprises a surface 212 which extends away from the main body 206. The surface 212 may comprise an opening 214 sized and shaped to receive set screw 216. A portion of the one-piece side tulip connector main body upper end 208 is separated from the bottom end 210 via space 218, thus forming a preexisting tulip or rod receiving channel sized and shaped to receive and hold therein a preexisting tulip 20 or rod 22.

The one-piece side tulip connector bottom end 210 comprises a preexisting pedicle screw engagement member 220 and a secondary tulip engaging member 222. The preexisting pedicle screw engagement member 220 is illustrated having two arms or finger-like projections 224 and 226 extending away from the one-piece side tulip connector 204 main body 206. The arms or finger-like projections 224 and 226 are separated by a space 228 of sufficient size to accommodate at least a portion of a preexisting pedicle screw threaded body 16 to rest or be placed therein. As shown, the arms or finger-like projections 224 and 226 are placed at or near where the preexisting pedicle screw threaded body 16 exits from the preexisting tulip 20 and resting under the preexisting tulip 20.

The secondary tulip engaging member 222 is illustrated herein as an extended platform or surface 230 extending away from the one-piece side tulip connector 204 main body 206 and in the opposite direction of the preexisting pedicle screw engagement member 220. An opening 232 rests within the extended platform or surface 230 and is sized and shaped to receive a tulip securing screw 234. The extended platform or surface 230 positions the secondary tulip 236 next to and in a side-by-side relationship with the preexisting tulip 20. In this position, a secondary rod may be attached to the preexisting tulip 20.

Referring to FIGS. 12A-12F, alternative embodiments of the add on screw system 100 utilizing a tulip within a tulip mechanism for securing a new tulip to an existing tulip are shown. In this embodiment, the add on screw system 100 includes a tulip-to-tulip connector, referred to as a tulip-to-tulip head attachment connector 238 or tulip-to-tulip head attachment connector 240. The tulip-to-tulip head attachment connector 238 is designed to engage with or secure to the bottom portion of the pre-existing tulip 20 which is secured to the preexisting threaded body 16 of the preexisting pedicle screw 14. The tulip-to-tulip head attachment connector 238 comprises an upper portion 242, a lower portion 244, and an intermediate portion 246 separating the upper portion 242 and the lower portion 244. The upper portion 242 is configured to engage with an add-on tulip head 248. The lower portion 244 is configured to engage with the pre-existing tulip 20.

Figure 12A:
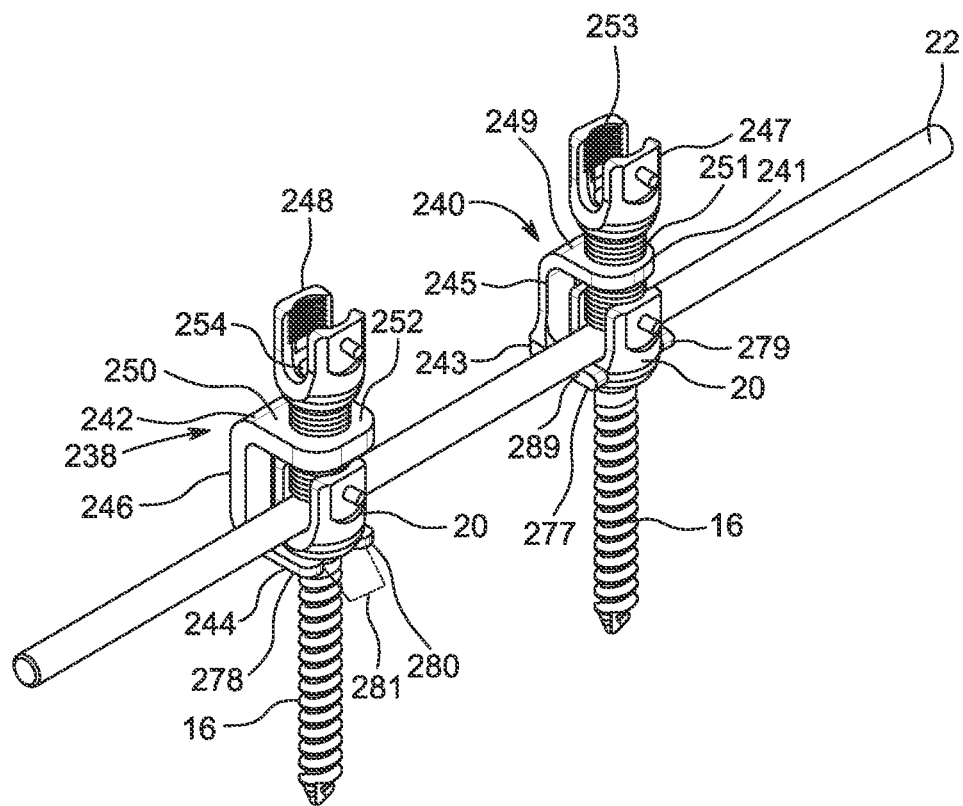
FIG. 12A is a perspective view of an alternative embodiment of the add on screw system utilizing a tulip within a tulip mechanism for securing a new tulip to an existing tulip.
Figure 12B:
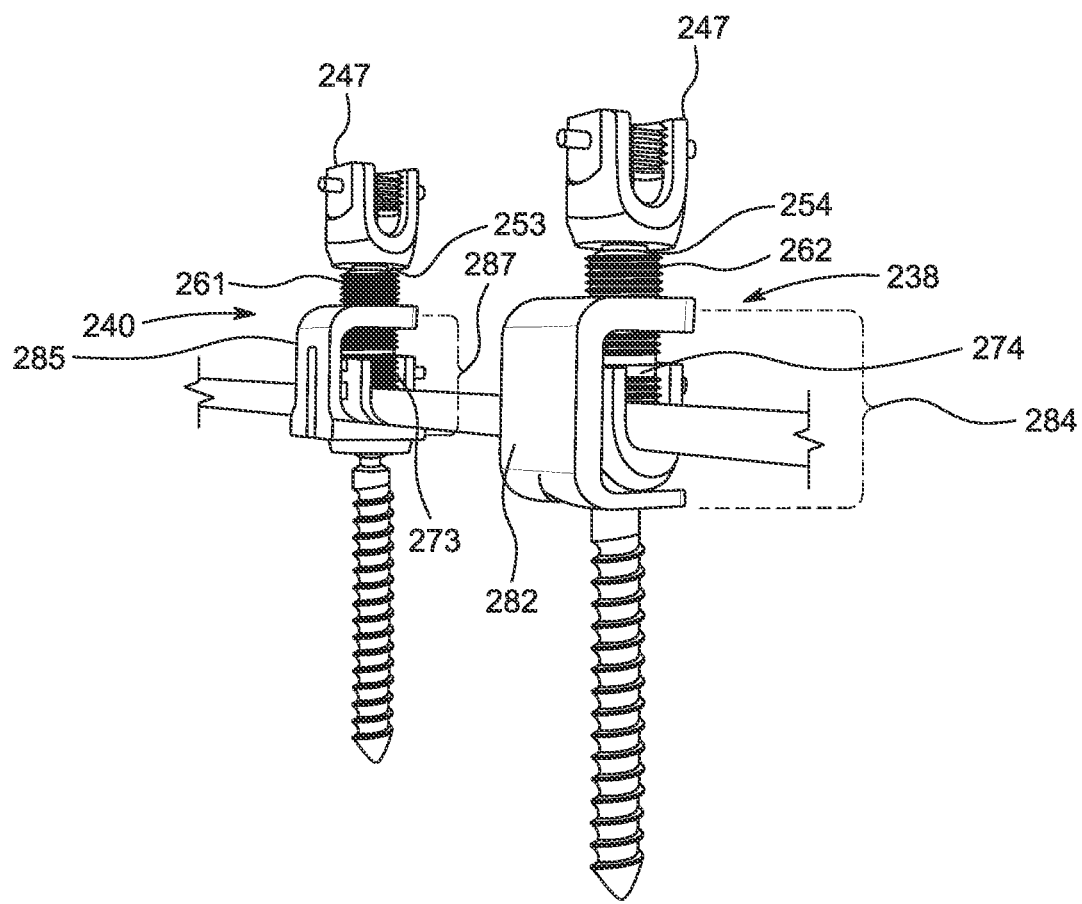
FIG. 12B is an alternative perspective view of the add on screw system illustrated in FIG. 12A.
Figure 12C:
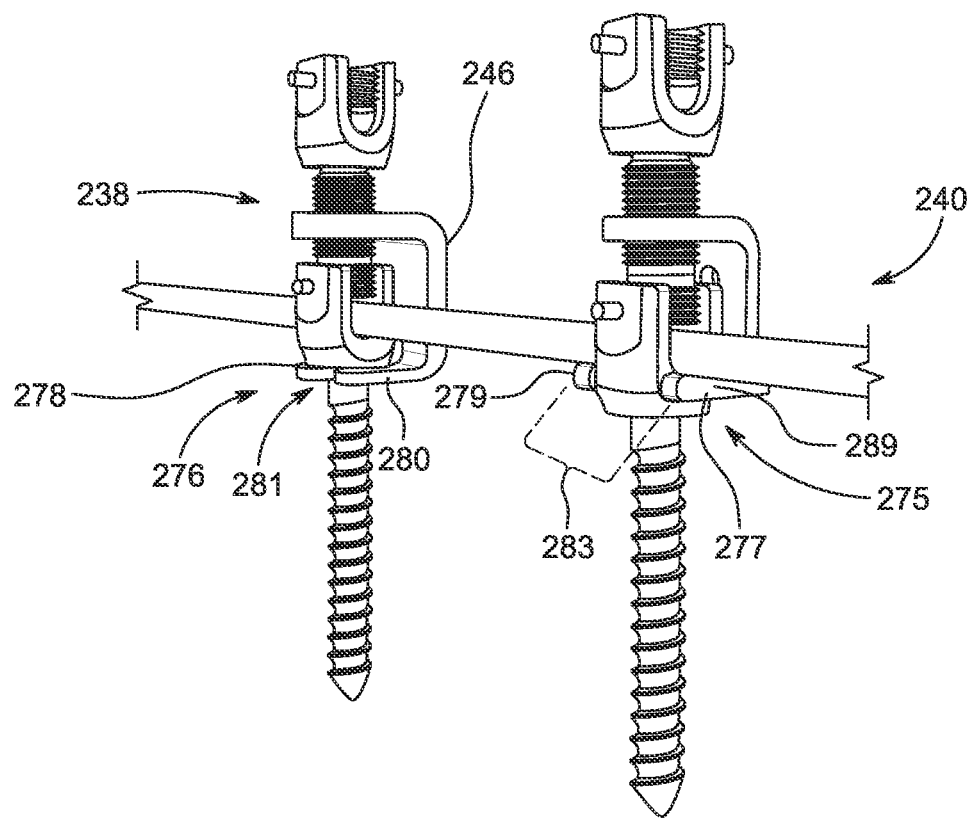
FIG. 12C is an alternative perspective view of the add on screw system illustrated in FIG. 12A.
Figure 12D:
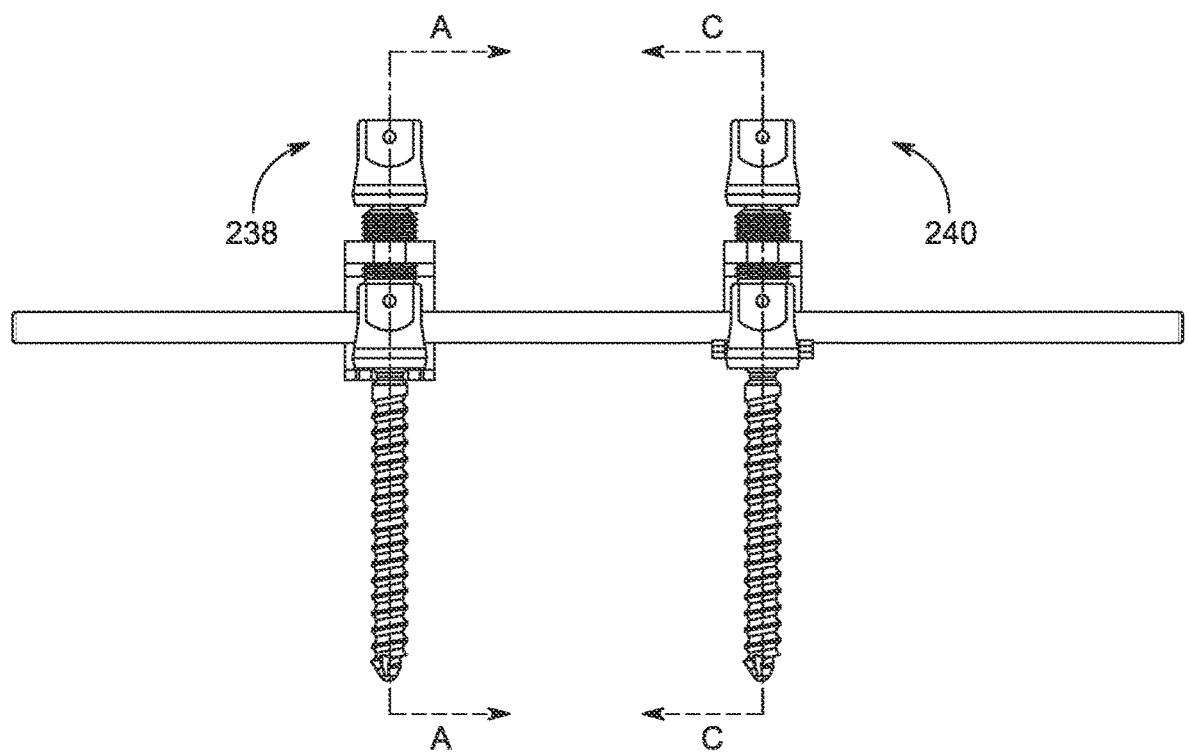
FIG. 12D is a plane view of the add on screw system illustrated in FIG. 12A.
Figure 12E:
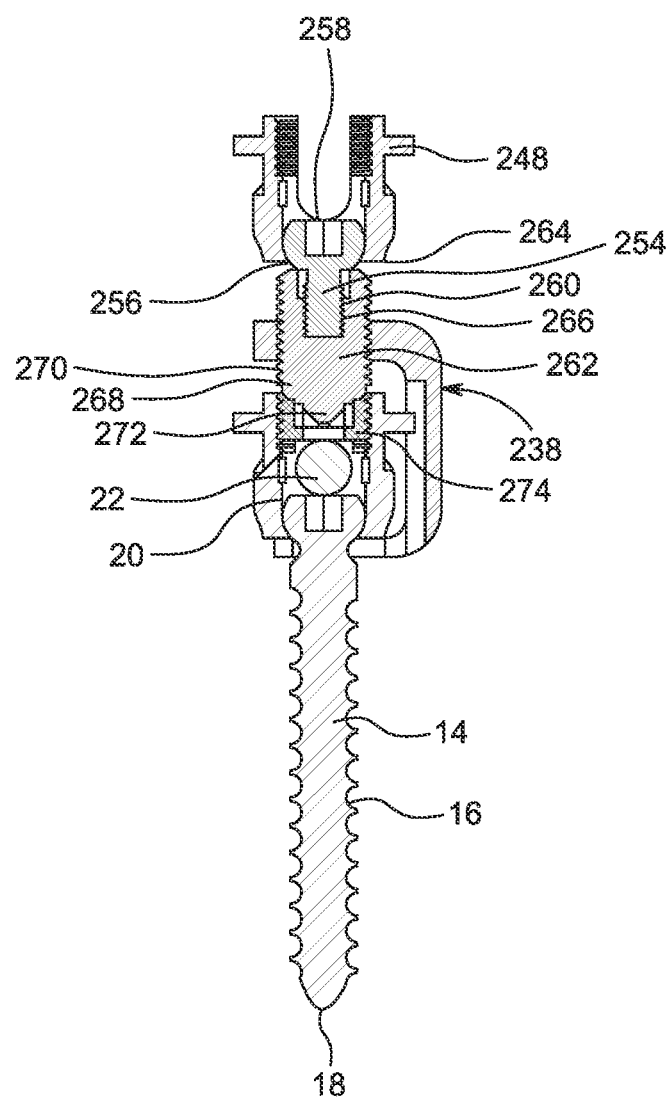
FIG. 12E is a cross section view of the add on screw system illustrated in FIG. 12A, taken along lines A-A in FIG. 12D.

The upper portion 242 comprises a surface 250 having an opening 252 sized and shaped to receive and hold therein an add-on spherical screw 254. The add-on spherical screw 254 is designed to fix the add-on tulip head 248 in place. As seen in FIG. 12E, the add-on spherical screw 254 includes an upper spherical body 256, sized and shaped to fit within a seat 258 of the add-on tulip head 248, and a threaded body 260. While illustrated as having a spherical body 256 to provide the add-on tulip head 248 polyaxial movement, the add-on spherical screw 254 may include an upper body having a different shape. The add-on spherical screw threaded body 260 is designed to secure to an attachment fixing set screw 262; the attachment fixing set screw 262 including an opening 264 with corresponding inner threading 266. The attachment fixing set screw 262 may include a body 268 having an outer threading 270, and terminating in a conical shaped end 272, thus allowing the attachment fixing set screw 262 to tighten a pre-existing tulip head set screw 274 secured within the preexisting tulip head 20.

The tulip-to-tulip head attachment connector lower portion 244 comprises a pre-existing tulip head engagement member 276. The pre-existing tulip head engagement member 276 may comprise a first member 278 and a second member 280, the first member 278 being separated from the second member 280 by a space, gap, or distance 281. The first member 278 may be an elongated body, or arm, extending away from the tulip-to-tulip head attachment connector intermediate portion 246. The second member 280 may be an elongated body, or arm, extending away from the tulip-to-tulip head attachment connector intermediate portion 246, and aligned in a generally parallel orientation relative to the first member 278, thus forming a generally L-shaped or J-shaped pre-existing tulip head engagement member 276.

The tulip-to-tulip head attachment connector intermediate portion 246 may include an elongated body or surface 282 separating the upper portion 242 and the lower portion 244 by a space or distance 284, thus forming a channel sufficient in size to receive the preexisting tulip head 20 therein.

The tulip-to-tulip head attachment connector 240 is designed to engage with or secure to the pre-existing rod 22 secured to the preexisting tulip head 20. The tulip-to-tulip head attachment connector 240 comprises an upper portion 241, a lower portion 243, and an intermediate portion 245 separating the upper portion 241 and the lower portion 243.

The upper portion 241 is configured to engage with an add-on tulip head 247. The lower portion 243 is configured to engage with the pre-existing rod 22.

Figure 12F:
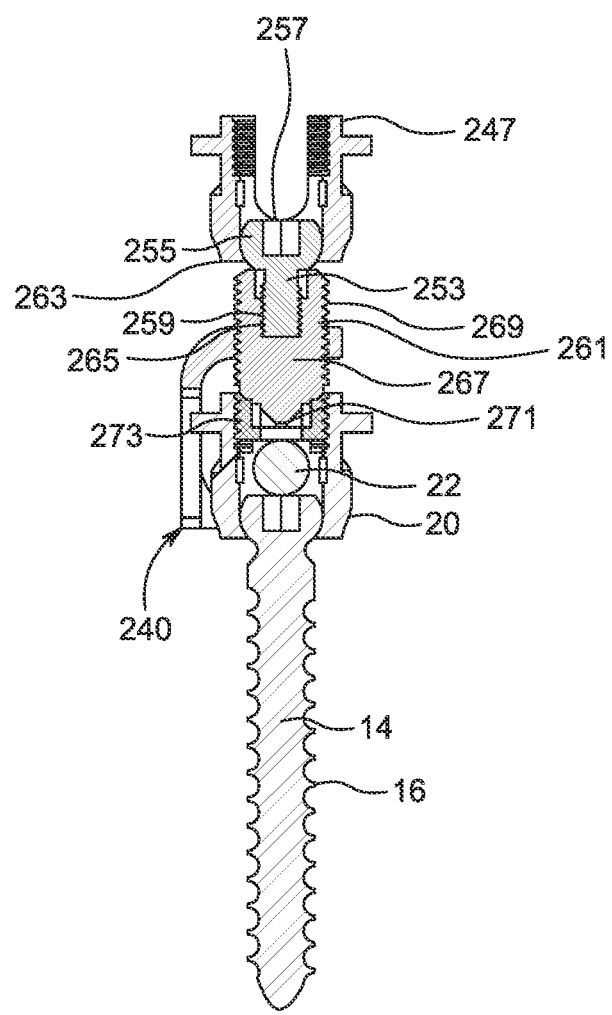
FIG. 12F is a cross section view of the add on screw system illustrated in FIG. 12A, taken along lines C-C in FIG. 12D.
Figure 13:
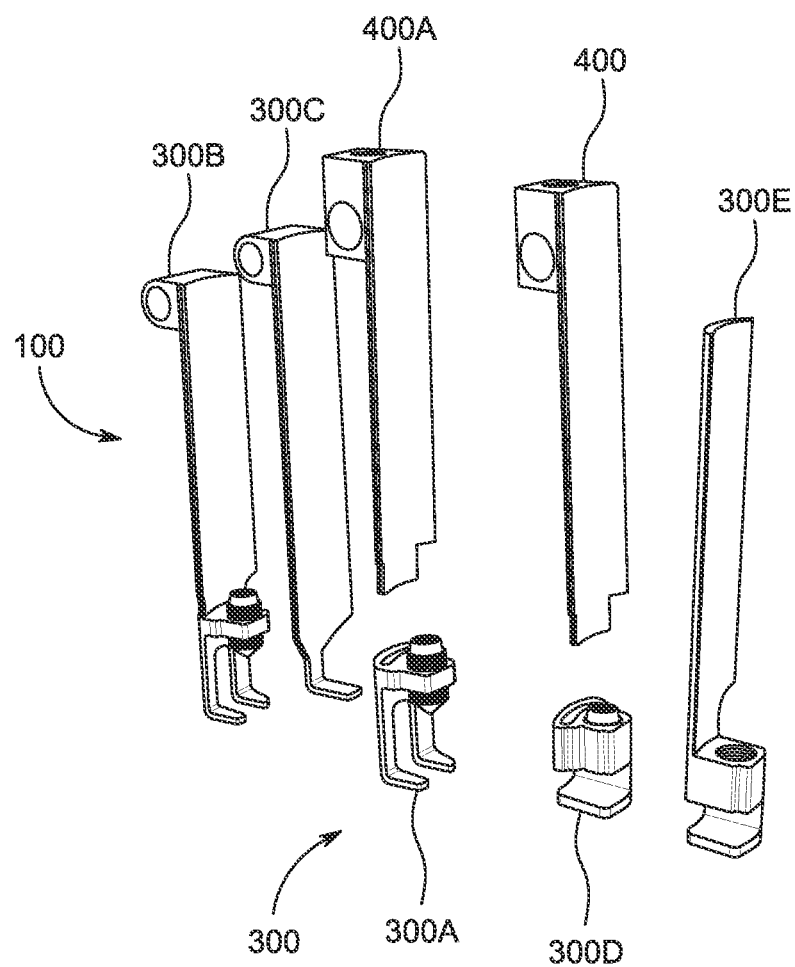
FIG. 13 is a perspective view of embodiments of the add-on screw system connectors and retractors.
Figure 14:
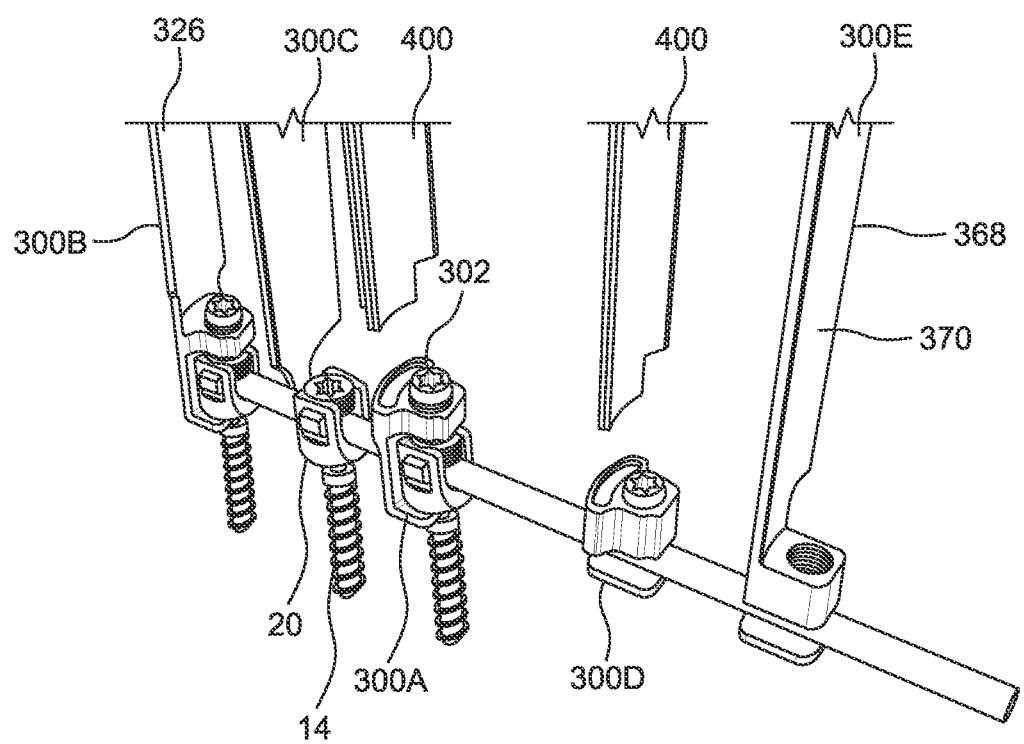
FIG. 14 is a perspective view of the embodiments of the add-on screw system connectors and retractors, shown interacting with preexisting pedicle screws or rods.
Figure 15:
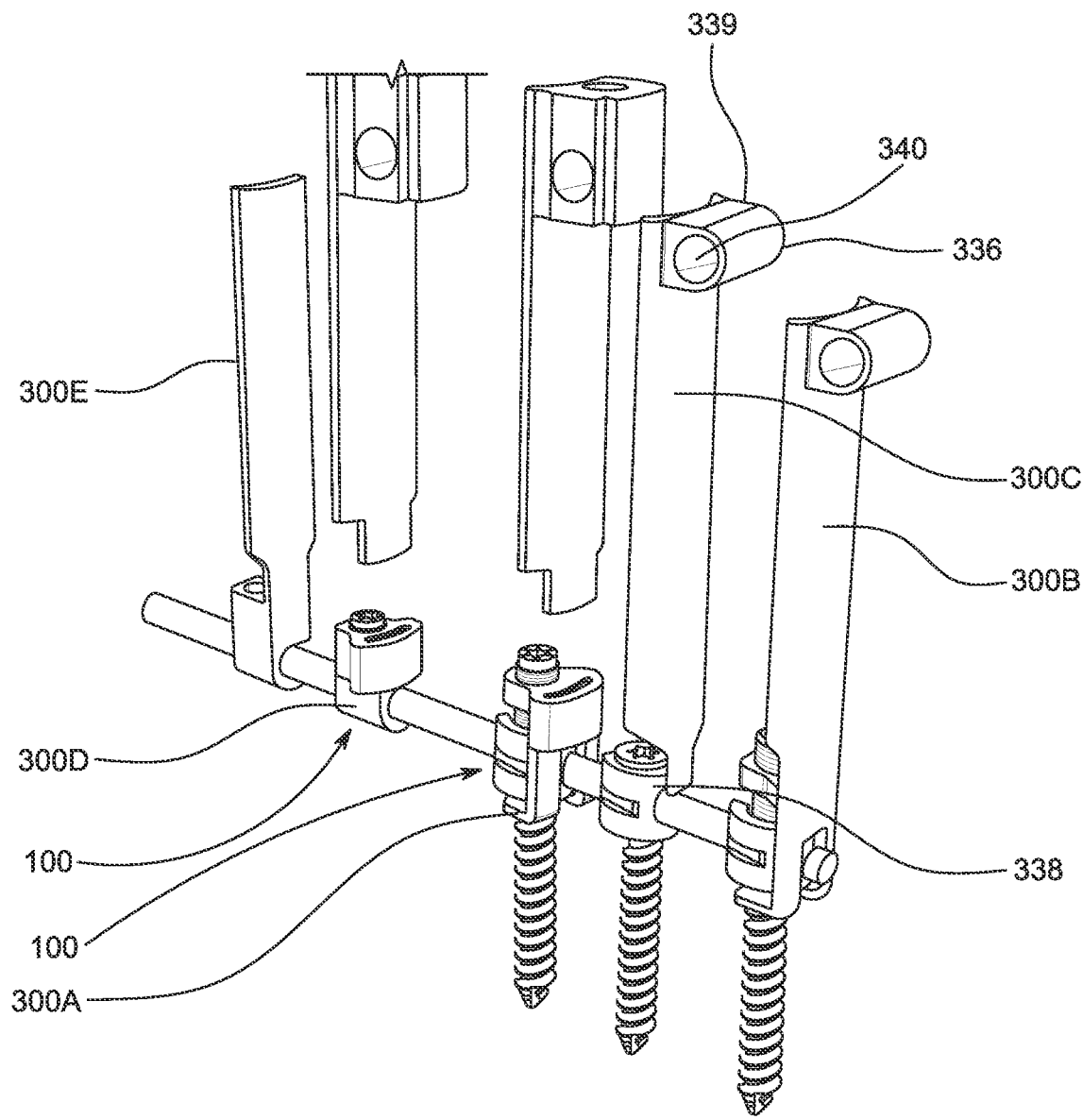
FIG. 15 is an alternative perspective view of the add-on screw system connectors and retractors illustrated in FIG. 14.
Figure 16:
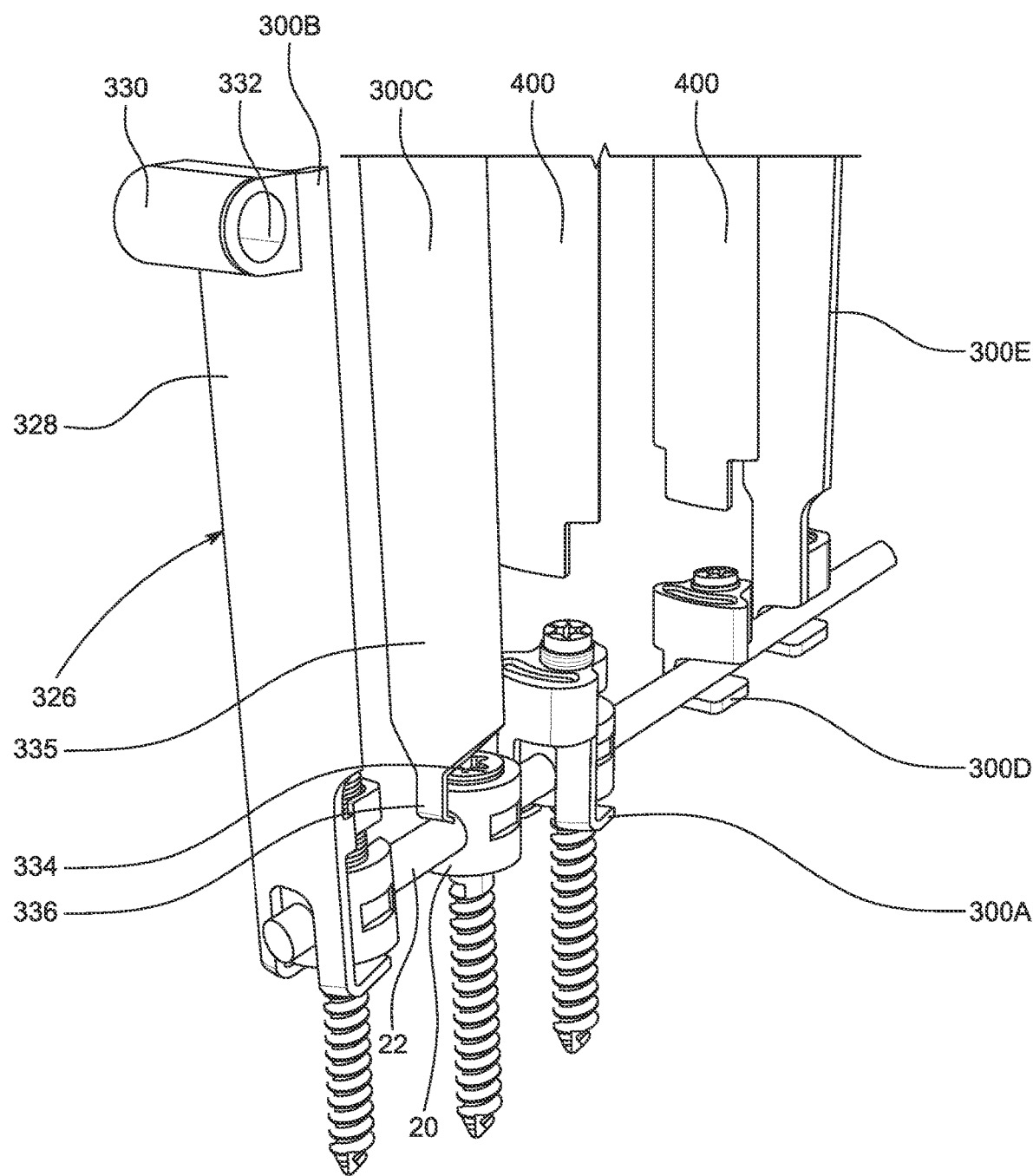
FIG. 16 is an alternative perspective view of the add-on screw system connectors and retractors illustrated in FIG. 14.
Figure 17:
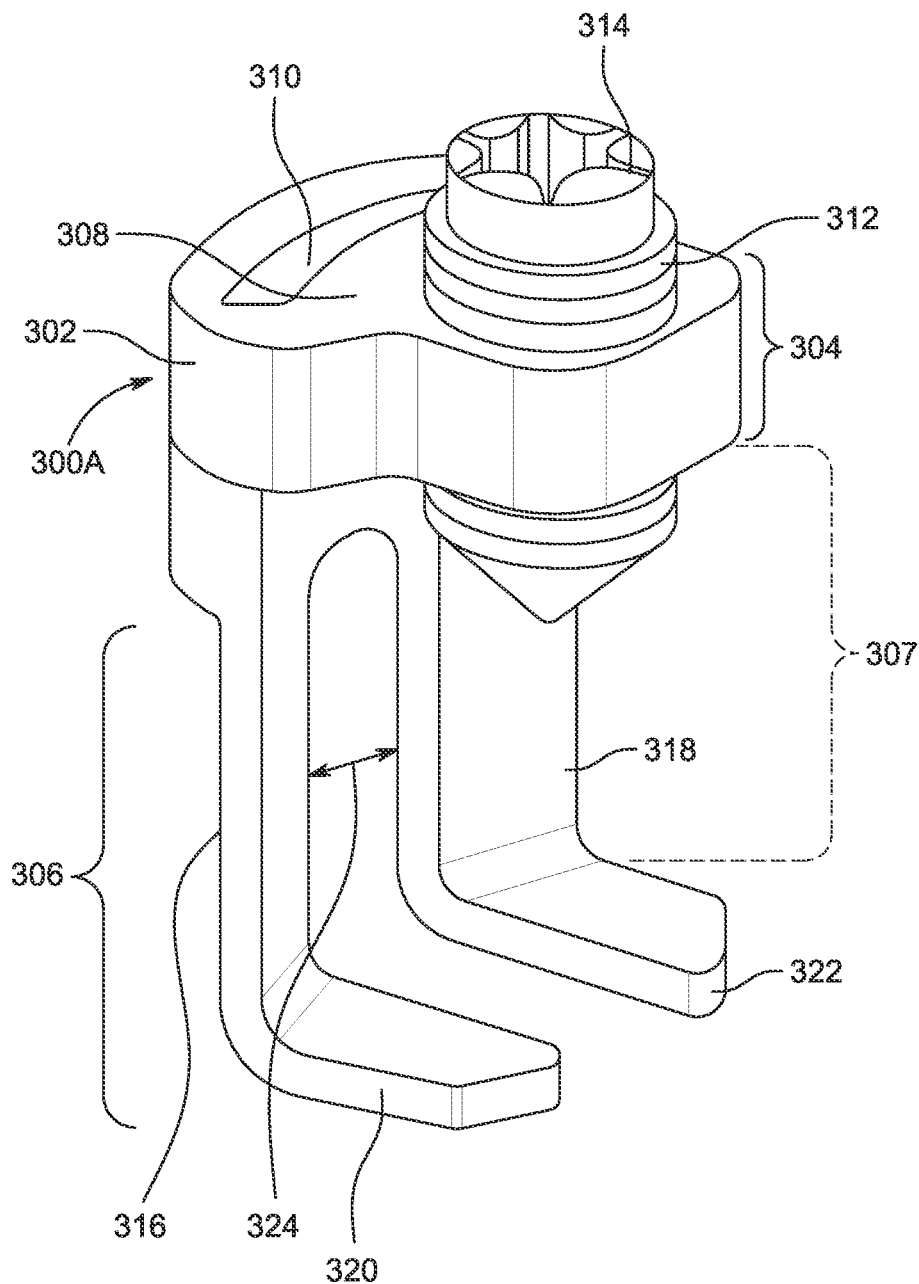
FIG. 17 is an illustrative embodiment of an add on screw system connector configured to engage with or secure to a pedicle screw tulip.
Figure 18:
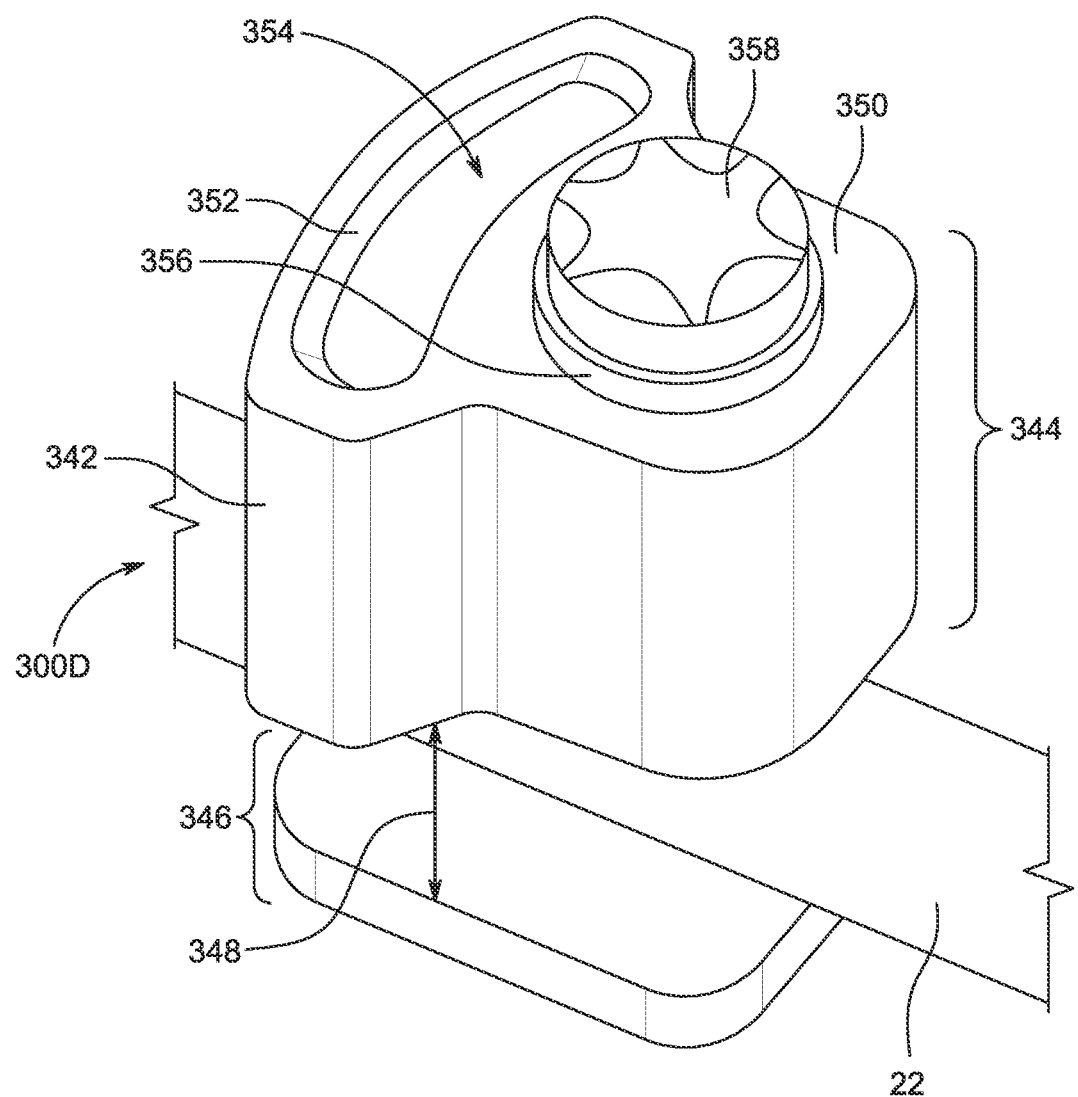
FIG. 18 is an illustrative embodiment of an add on screw system connector configured to engage with or secure to a surgical rod.
Figure 19:
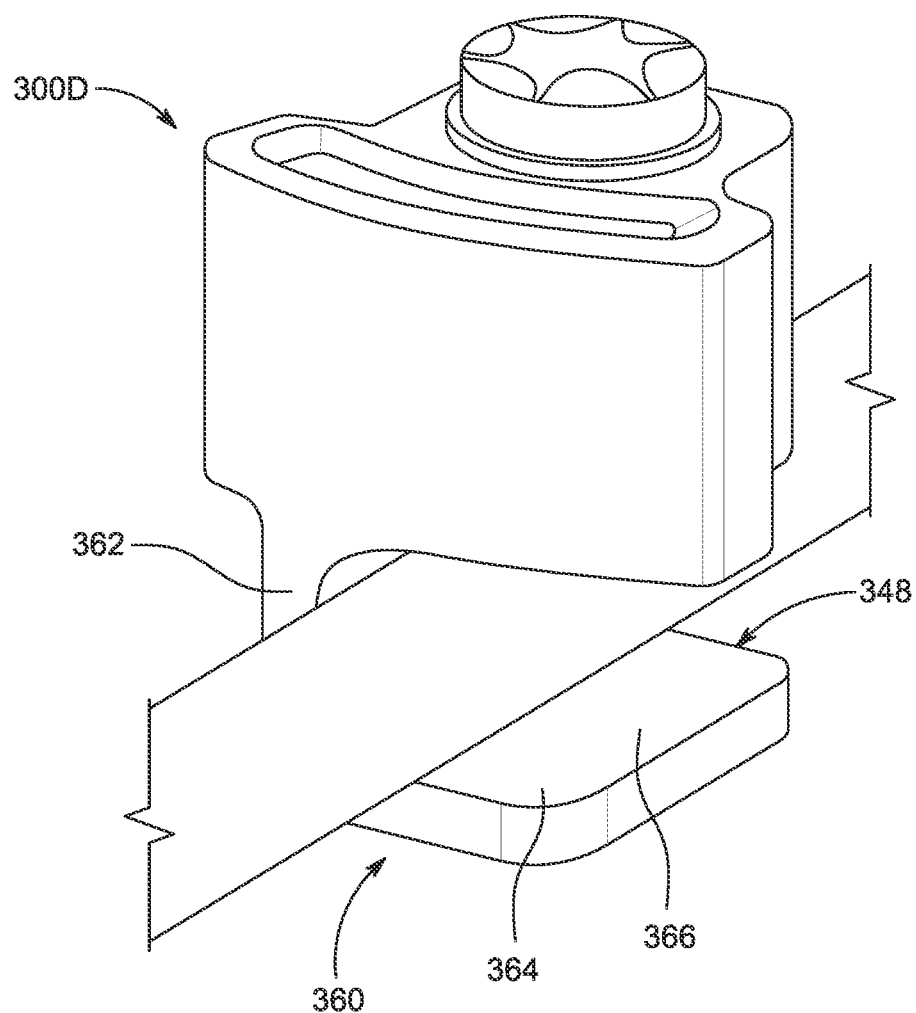
FIG. 19 is an alternative view of the add on screw system connector shown in FIG. 18.

The upper portion 241 comprises a surface 249 having an opening 251 sized and shaped to receive and hold therein an add-on spherical screw 253. The add-on spherical screw 253 is designed to fix the add-on tulip head 247 in place. As seen in FIG. 12F, the add-on spherical screw 253 includes an upper spherical body 255, sized and shaped to fit within a seat 257 of the add-on tulip head 247, and a threaded body 259. While illustrated as having a spherical body 255 to provide the add-on tulip head 247 polyaxial movement, the add-on spherical screw 253 may include a body having a different shape. The add-on spherical screw threaded body 259 is designed to secure to an attachment fixing set screw 261. The attachment fixing set screw 261 includes an opening 263 with corresponding inner threading 265. The attachment fixing set screw 261 may include a body 267 having an outer threading 269, and terminating in a conical shaped end 271, thus allowing the attachment fixing set screw 261 to tighten a pre-existing tulip head set screw 273 secured within the preexisting tulip head 20.

The tulip-to-tulip head attachment connector lower portion 243 comprises a pre-existing tulip head engagement member 275. The pre-existing tulip head engagement member 275 may comprise a first member 277 and a second member 279, the first member 277 being separated from the second member 279 by a space, gap, or distance 283. The first member 277 may be an elongated body, or arm, extending away from tulip-to-tulip head attachment connector intermediate portion 245. The second member 279 may be an elongated body, or arm, extending away from tulip-to-tulip head attachment connector intermediate portion 245, and aligned in a generally parallel orientation relative to the first member 277, thus forming a generally L-shaped or J-shaped pre-existing tulip head engagement member 275.

The tulip-to-tulip head attachment connector intermediate portion 245 may include an elongated body or surface 285 separating the upper portion 241 and the lower portion 243 by a space or distance), thus forming a channel sufficient in size to receive the preexisting tulip head 20 therein. The tulip-to-tulip head attachment connector intermediate portion 245 may also include a cut out section, or channel 287.

To aid in attaching to the preexisting rod 22, the pre-existing tulip head engagement member first member 277 and second member 279 may include a preexisting rod receiving member 289, illustrated herein as a dimple or indentation. The preexisting rod receiving member 289 is sized and shaped to correspond with the curvature of the preexisting rod 22, thus providing a secure, snug, and level fit between the two.

Referring to FIGS. 13-16, the add on screw system 100 may also comprise one or both of a connector, referred to generally as add on screw system connector 300, or individually as add on screw connectors 300A, 300B, 300C, 300D, 300E or the like, and a retractor, referred to generally as add on screw system retractor blade 400. The add on screw system connector 300 is configured to secure to an existing pedicle screw previously implanted into a patient and/or to a previously implanted rod at one end and secure to or include a retractor blade. The add on screw system connector 300A may comprise a main body 302 having an upper portion 304 configured to engage with pedicle screw set screw and/or a retractor blade, and a lower portion 306 configured to engage with a preexisting surgical device, such as a previously implanted pedicle screw tulip 20. The add on screw system connector main body upper portion 304 is separated from the add on screw system connector main body lower portion 306 by a space or channel 307. The space or channel 307 is sized and shaped to allow an existing pedicle screw tulip 20 previously implanted into a patient to fit and or rest therein.

The add on screw system connector main body 302 upper portion 304 comprises an upper surface 308 having a retractor blade receiving member 310. The retractor blade receiving member 310 is illustrated as an opening sized and shaped to receive and hold therein at least a portion of a retractor blade, such as add on screw system retractor blades 400A. A secondary opening 312 is sized and shaped to receive a set screw 314, which, when in use, allows the add on screw system connector 300 to secure to the existing pedicle screw tulip 20 previously implanted into a patient.

The add on screw system connector 300A main body lower portion 306 includes two arms or finger-like extensions 316 and 318, extending or oriented in a direction down or away from the add on screw system connector main body 302. The two arms or finger-like extensions 316 and 318 may terminate in pedicle screw system engaging members 320 and 322, illustrated herein as hook shaped ends. The two arms or finger-like extensions 316 and 318 may be arranged in a parallel manner and separated by a space or distance 324. The space or distance 324 is sufficient to allow the arms or finger-like extension pedicle screw system engaging members 320 and 322 to engage with or secure to two different positions along or to the existing pedicle screw tulip 20 previously implanted into a patient. Preferably, the two arms or finger-like extensions 316 and 318 are arranged and oriented to allow the arms or finger-like extension pedicle screw system engaging members 320 and 322 to engage with or secure to the bottom of the tulip 20 (or rod 22), or to the area where the pedicle screw threaded body 16 meets or extends out from the tulip 20 (or rod 22). While the add on screw system connector 300A is shown with two arms or finger-like extensions 316 and 318, an alternative embodiment may include a single arm or finger-like extension 316 or 318.

The add on screw system connector 300B includes all the same structural components as that described for the add on screw system connector 300A except for the inclusion of the retractor blade receiving member 310. As an alternative, the add on screw system connector 300B comprises a retractor blade 326 integrally formed therein. The retractor blade 326 includes an elongated body 328, terminating in a mounting structure 330 having an opening 332 (see FIG. 16). The mounting structure 330 allows the securing of the retractor blade 326 to a structure outside of the patient.

The add on screw system connector 300C is configured to secure to the area where the set screw 334 rests inside the tulip 20, resting above the preexisting rod 22. Accordingly, the add on screw system connector 300C includes an elongated body 335 having a pedicle screw system engaging member 336 at one end. The pedicle screw system engaging member 336 includes an L-shaped member 338 sized and shaped to fit within the area where the set screw 334 rests inside the preexisting tulip 20. At or along the opposite end of the elongated body 336, the add on screw system connector 300C may include a mounting structure 339 having an opening 340.

The add on screw system connector 300D is configured to engage with and secure to a previously implanted rod 22. The add on screw system connector 300D may comprise a main body 342 having an upper portion 344 configured to engage with pedicle screw set screw and retractor blade, and a lower portion 346 configured to engage with a preexisting surgical device, such as a previously implanted rod 22. The add on screw system connector main body upper portion 344 is separated from the add on screw system connector main body lower portion 346 by a space 348 defining a channel sized and shaped to receive a portion of the rod 22 previously implanted into a patient to fit and rest therein.

The add on screw system connector main body upper portion 344 comprises an upper surface 350 having a retractor blade receiving member 352. The retractor blade receiving member 352 is illustrated as an opening 354 sized and shaped to receive and hold therein at least a portion of a retractor blade, such as the add on screw system retractor blades 400. A secondary opening 356, preferably threaded, is sized and shaped to receive a set screw 358, which, when in use, allows the add on screw system connector 300D to secure to the rod 22. The add on screw system connector main body lower portion 346 includes a rod engagement member 360, illustrated herein as a first member 362 and a second member 364, where the first member 362 is an elongated body extending down or away from the screw system connector main body 342. The second member 364 may comprise a surface 366 aligned in a perpendicular or angled relationship to the first member 362, thus forming an L-shaped or J-shaped end.

The add on screw system connector 300E includes all the same structural components as that described for the add on screw system connector 300D except for the inclusion of the retractor blade receiving member 352. As an alternative, the add on screw system connector 300E comprises a retractor blade 368 integrally formed therein. The retractor blade 368 includes an elongated body 370. The elongated body 370 may terminate in a mounting structure, similar to mounting structure 330.

Figure 20:
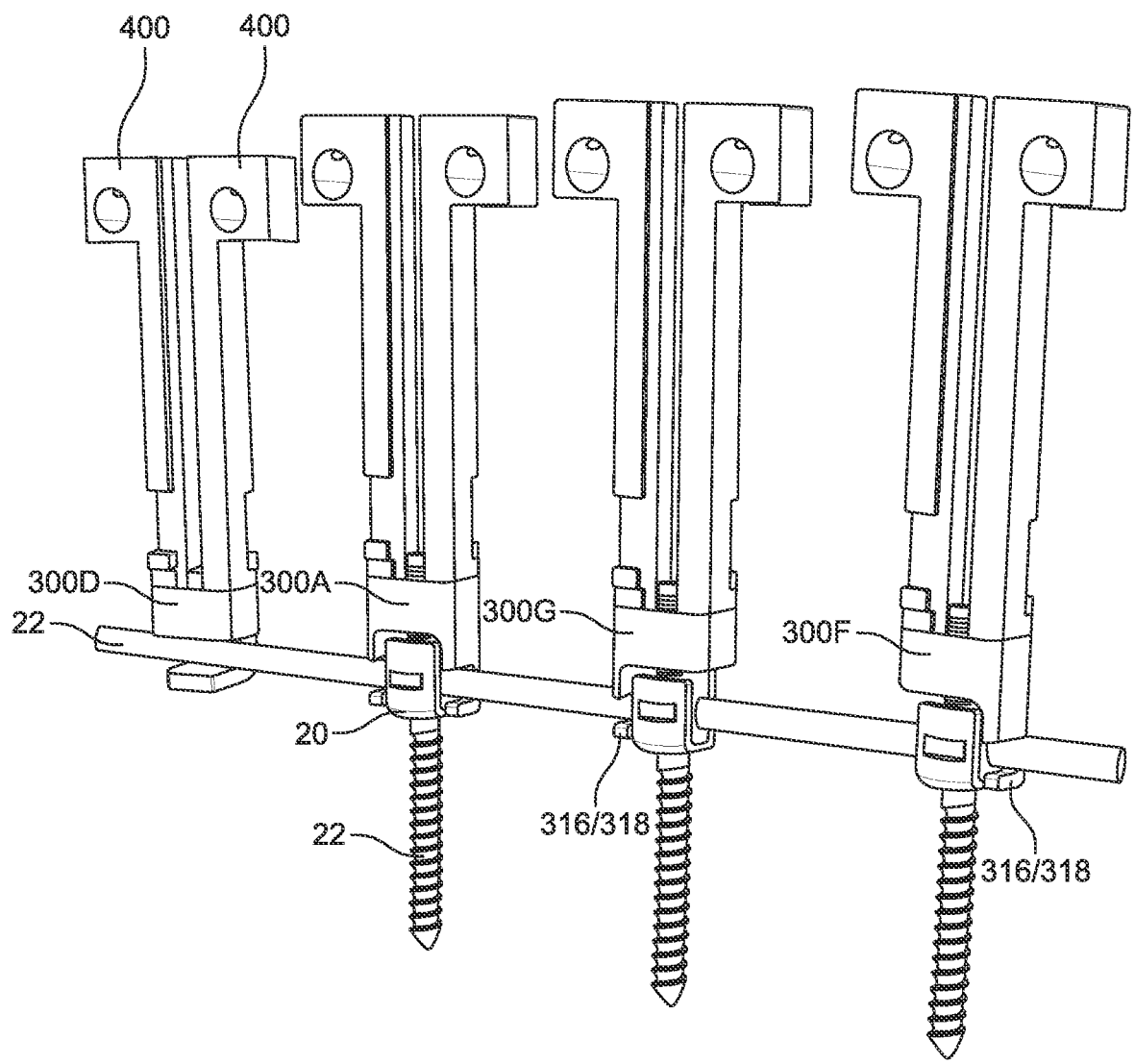
FIG. 20 illustrates the add on screw system connectors secured with multiple retractor blades.
Figure 21:
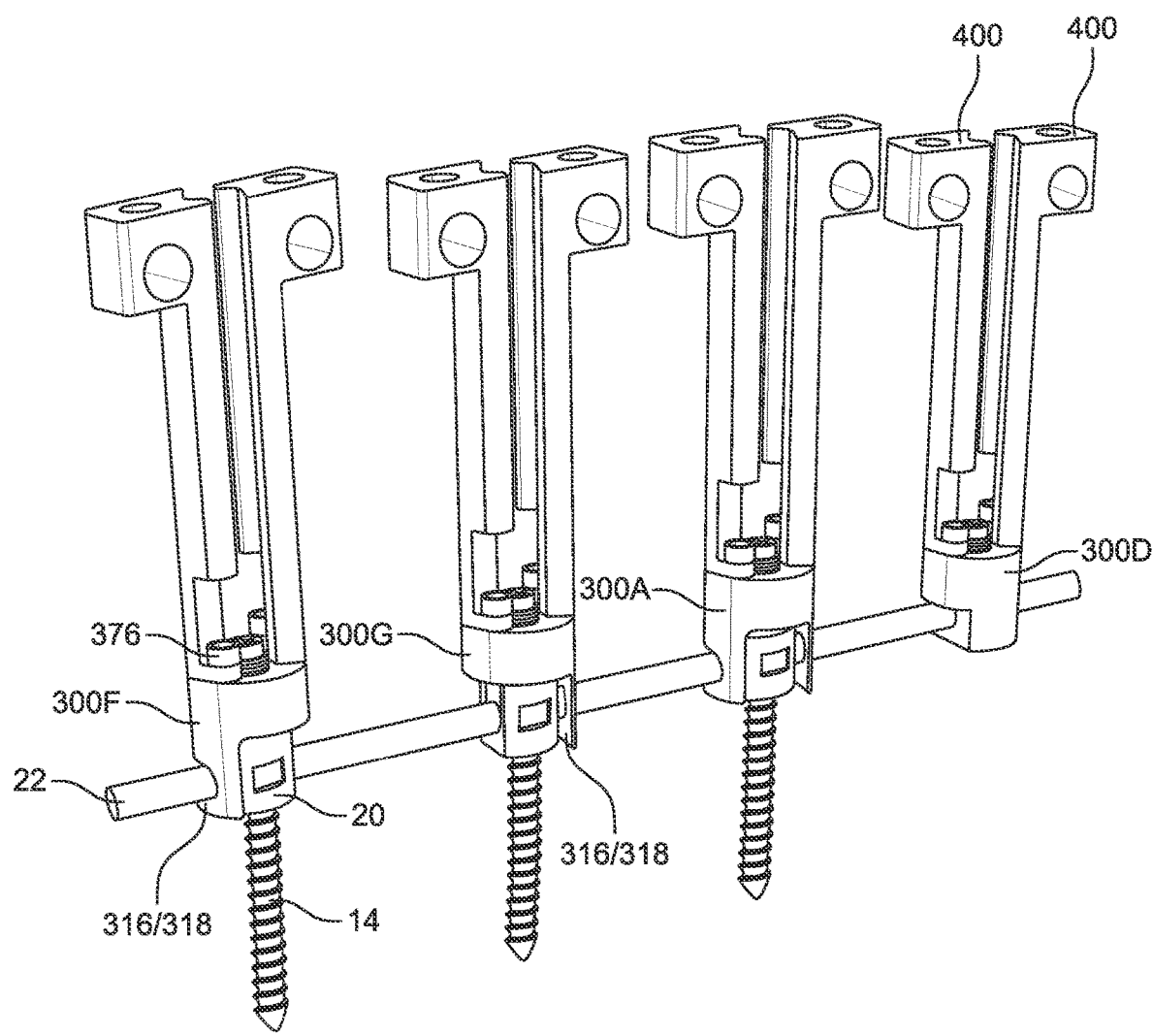
FIG. 21 is an alternative view of the add on screw system connectors secured with multiple retractor blades shown in FIG. 20.
Figure 22A:
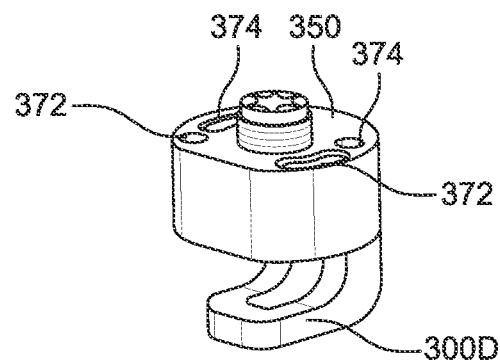
FIG. 22A illustrates an embodiment of the add on screw system connector adapted to secure with multiple retractor blades.
Figure 22B:
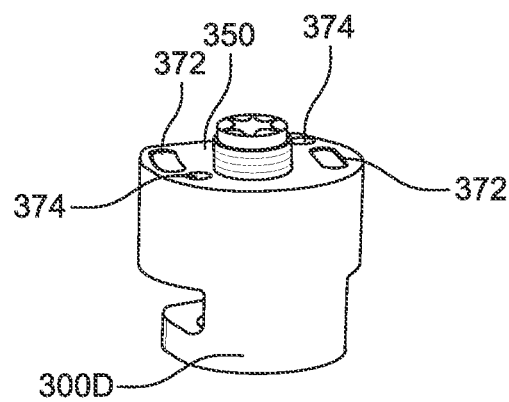
FIG. 22B illustrates an alternative view of the connector shown in FIG. 22A.
Figure 23A:
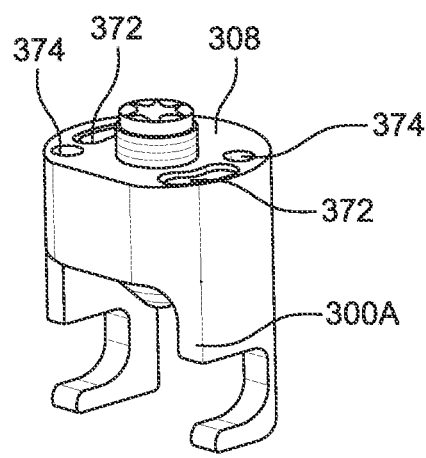
FIG. 23A illustrates an embodiment of the add on screw system connector adapted to secure with multiple retractor blades.
Figure 23B:
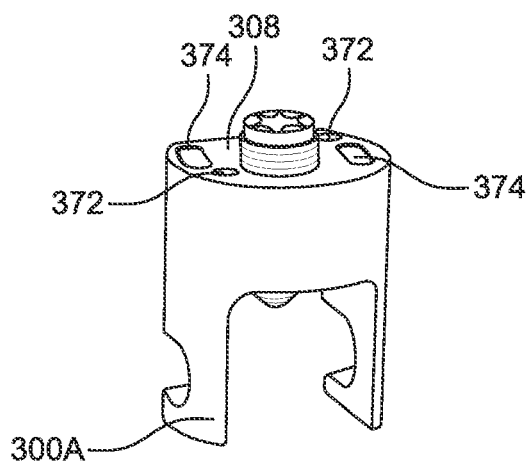
FIG. 23B illustrates an alternative view of the connector shown in FIG. 23A.
Figure 24A:
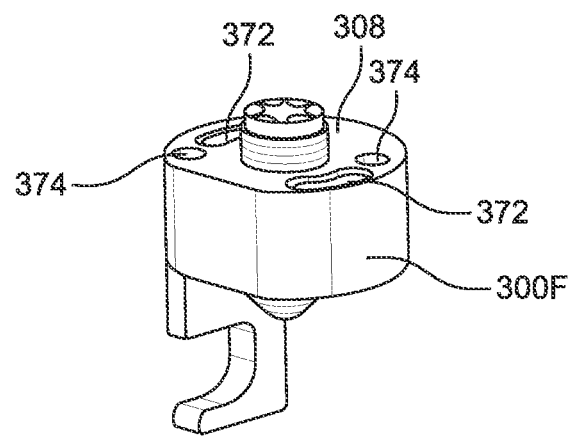
FIG. 24A illustrates an embodiment of the add on screw system connector adapted to secure with multiple retractor blades.
Figure 24B:
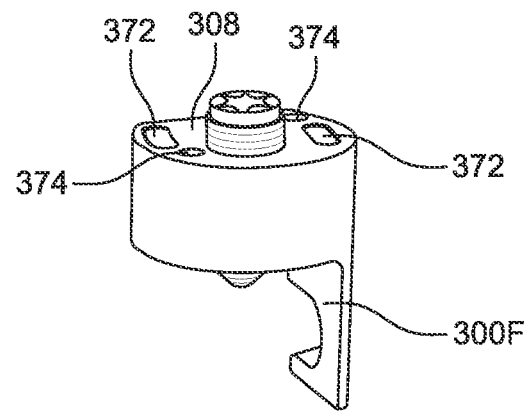
FIG. 24B illustrates an alternative view of the connector shown in FIG. 24A.
Figure 25A:
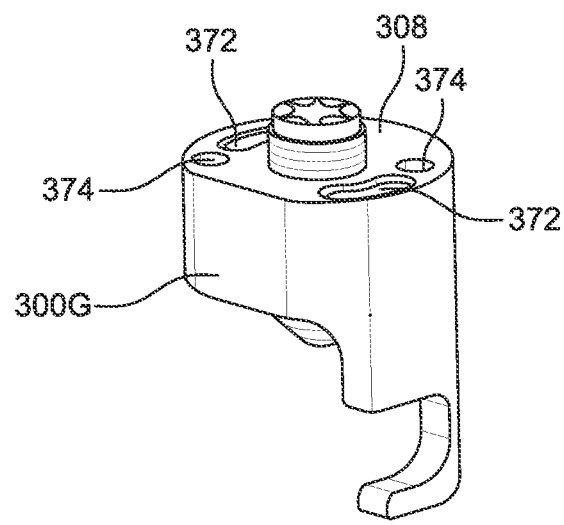
FIG. 25A illustrates an embodiment of the add on screw system connector adapted to secure with multiple retractor blades.
Figure 25B:
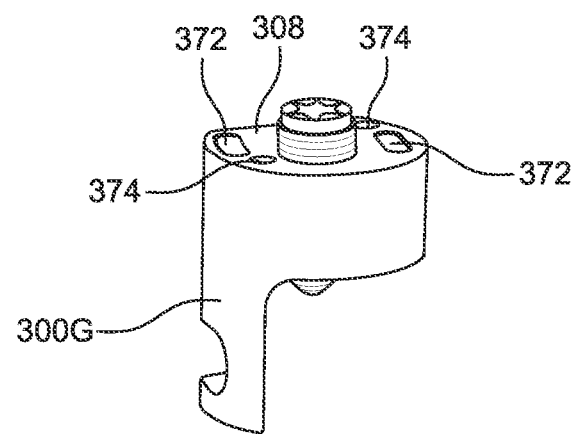
FIG. 25B illustrates an alternative view of the connector shown in FIG. 25A.

The add on screw system connectors 300 illustrated in FIGS. 13-19 are shown to include attachment with single retractor blade 400. However, the add on screw system connectors 300 may be adapted to secure with two retractor blades 400. FIGS. 20 and 21 illustrate embodiments of the add on screw system connectors 300A and 300D confirmed for multiple retractors. In addition, the figures include the add on screw system connectors 300A having a single left (300F) or right (300G) arms or finger-like extensions 316 or 318. FIGS. 22A-25B illustrate the add on screw system connectors 300 with the retractor blades 400 attached thereto. As shown, the upper surfaces (308 or 350) comprise multiple openings, two openings 372 for engagement (receiving) with a portion of the retractor blade 400 and two smaller openings for receiving screws 376, see FIG. 21.

Figure 27:
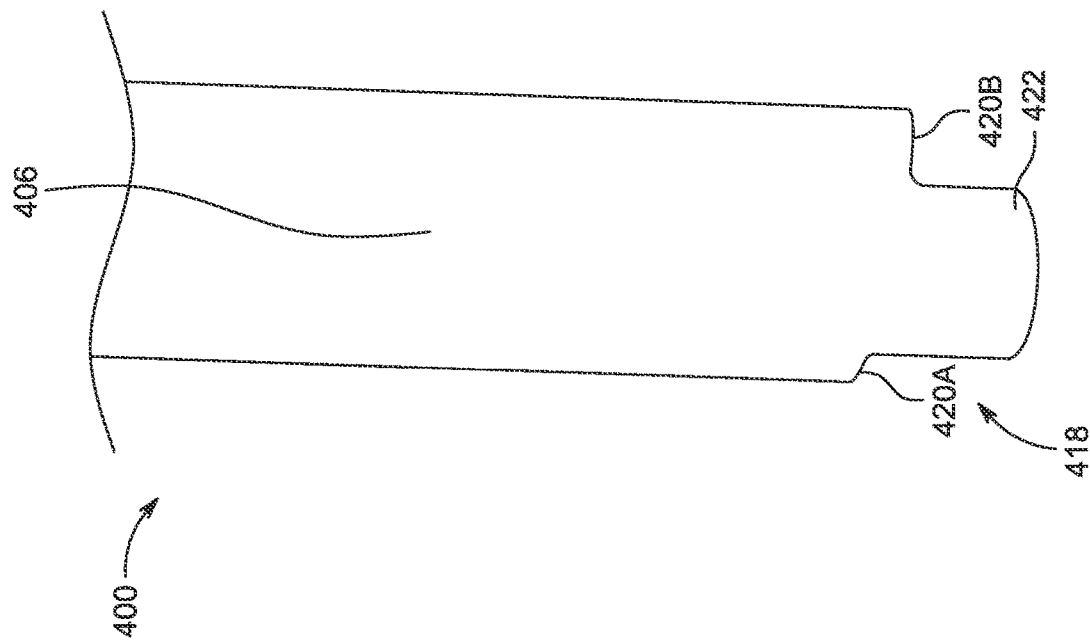
FIG. 27 is an alternative partial view of the retractor blade shown in FIG. 26.
Figure 26:
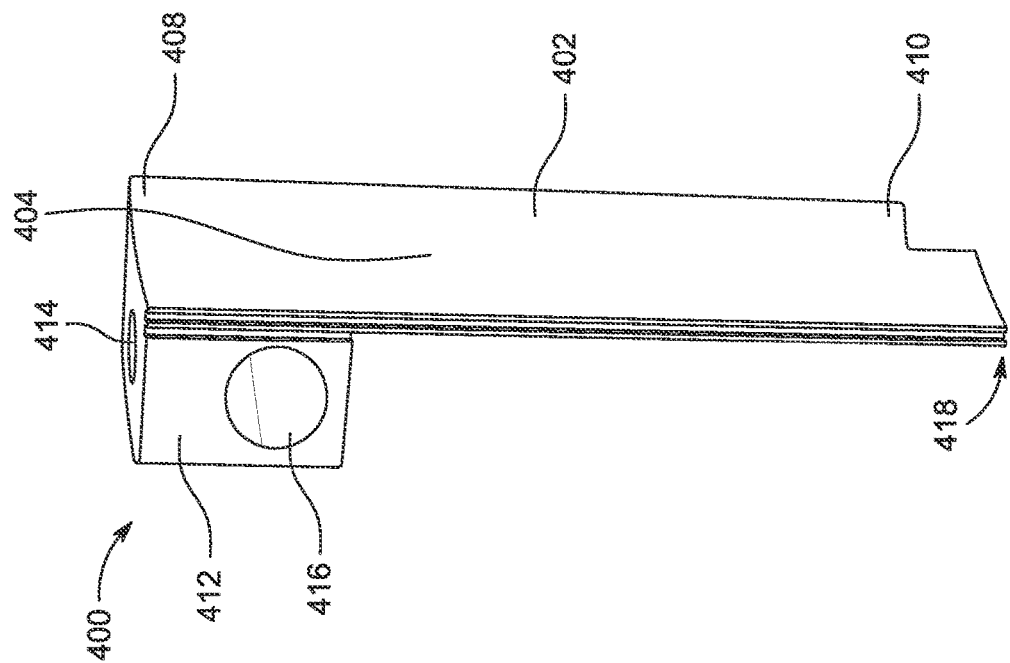
FIG. 26 is a perspective view of an illustrative embodiment of a retractor blade.

Referring to FIGS. 26 and 27, an embodiment of the retractor blade 400 is shown. The retractor blade 400 may include a main body 402 having an inner surface 404 and an outer surface 406. The retractor blade main body 402 includes a first upper end 408, and an opposing, second or lower end 410. At or along the upper end, the retractor blade 400 may include a mounting structure 412 having a top opening 414 and side opening 416. The lower end 410 includes a connector engaging member 418, sized and shaped to fit within and secure to connector add on screw system connector, i.e., fitting into the add on screw system connector main body retractor blade receiving member 310, or similar structures. The connector engaging member 418 may have shoulders 420A and 420B and tab 420. When the tab 420 is inserted into the add on screw system connector main body retractor blade receiving member 310, shoulders 420A and 420B rest on the upper surface (i.e., 308 or 350) of the add on screw system connector 300.

In use, generally, as an add-on surgical procedure to add additional surgical hardware, i.e., a surgical rod to existing implants, during exposure, the existing bone screw and rod at the surgical site will be exposed. The add on screw system connector 300 will be placed either around the rod or screw head, allowing the surgeon to attach a retractor plate or blade (such as retractor blade 400) to it for surgical exposure. During the surgery, the surgeon will then be able to distract off the add on screw system 100 to an adjacent bone screw at the level above and/or below that does not have a pre-existing screw and will be part of the new fusion site. Once the add on screw system connector 300 is attached to the pre-existing screw head and/or rod, a retractor blade (such as retractor blade 400) can be attached to aid in exposure. Once the exposure is performed, this attachment is removed. A tulip, polyaxial, or monoaxial, or any type of screw head or connector, will be inserted either attached directly to the pre-existing bone screw head and/or rod connection or with an add on screw system connector 300 attached to the pre-existing screw head or attached rod with a screw head attached to it, allowing connection to an adjacent vertebral screw by rod insertion above and/or below that vertebrae.

Figure 28:
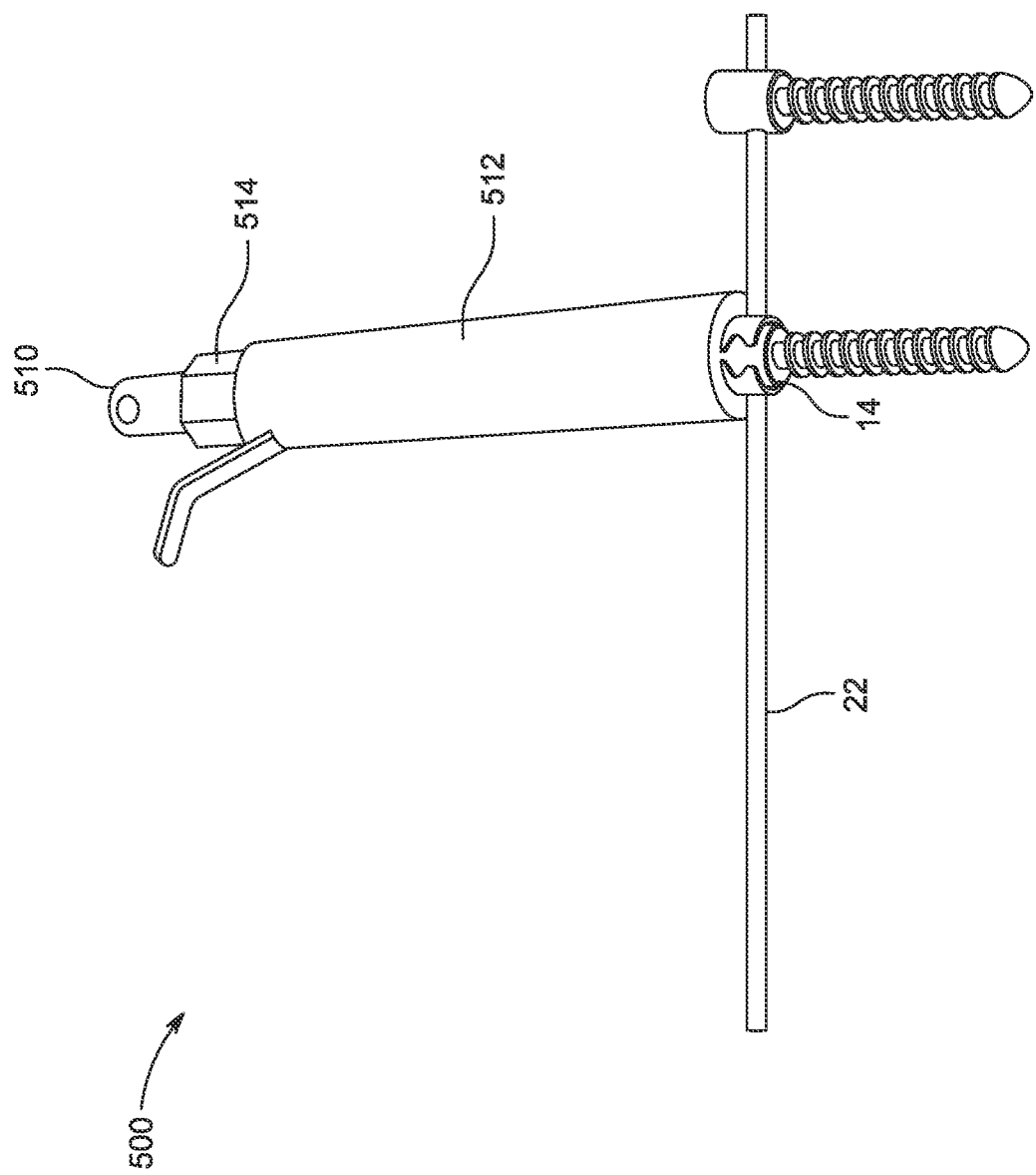
FIG. 28 is a perspective view of a tower assembly.
Figure 29:
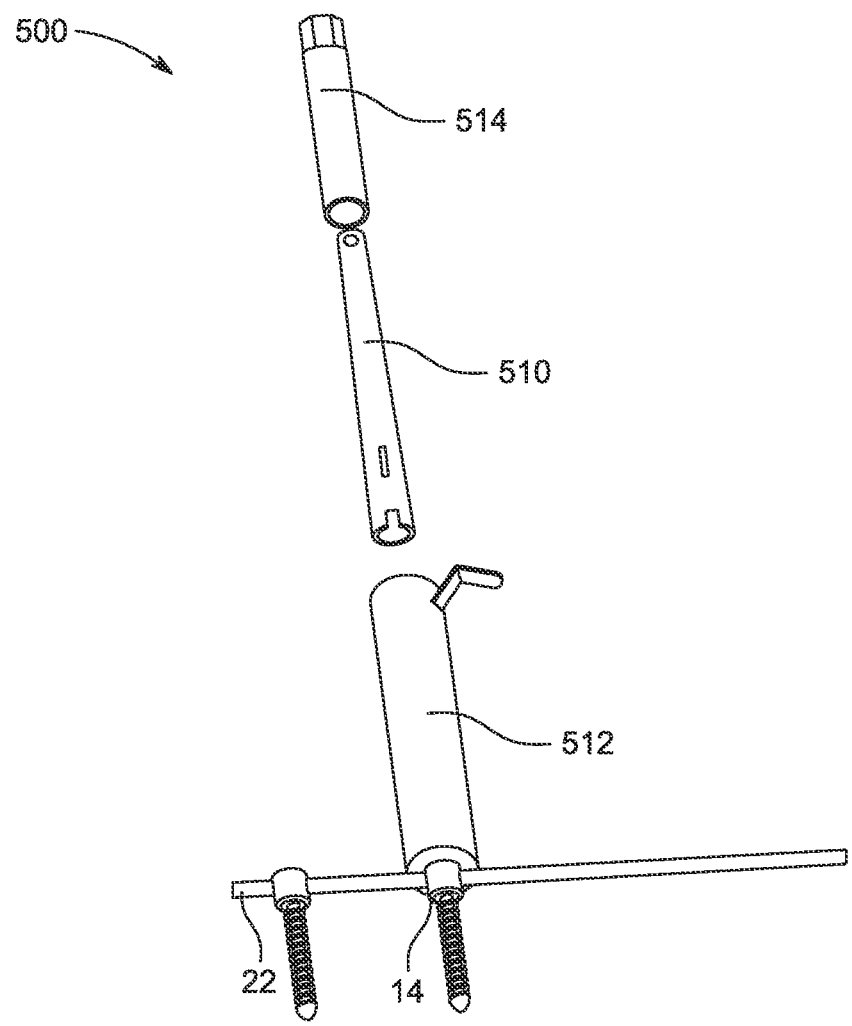
FIG. 29 is an exploded view of the tower assembly.

Referring to FIGS. 28-41, an illustrative embodiment of a tower assembly 500 is shown. The tower assembly 500 comprises one or more components, in any combination, i.e., any one component, any two components, or all three components, including an inner member, referred to as a 510 tower, an outer member, referred to as a dilator 512, and an intermediate member, referred to as a locking sleeve 514. The tower assembly 500 is configured to engage with and/or secure to a preexisting portion of a pedicle screw, preferably at or along the tulip portion. Referring to FIG. 28 or FIG. 29, the tower assembly 500 is shown engaging with and secured to the pedicle screw 14. The pedicle screw 14 is secured to the rod 22. A portion of the tower assembly 500 may be configured to secure or interact with the one or more add on screw systems described above.

Figure 30:
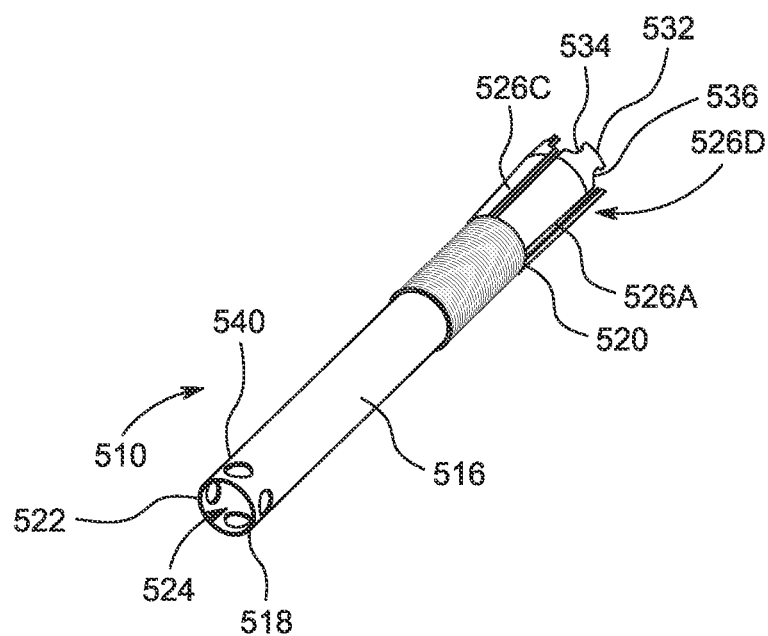
FIG. 30 is a perspective view of an illustrative embodiment of a tower of the tower assembly.
Figure 31:
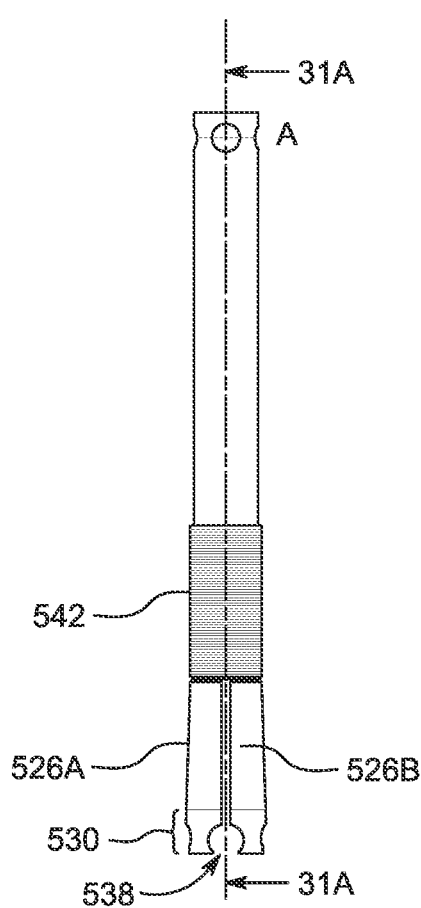
FIG. 31 is a side view of the tower illustrated in FIG. 30.
Figure 32:
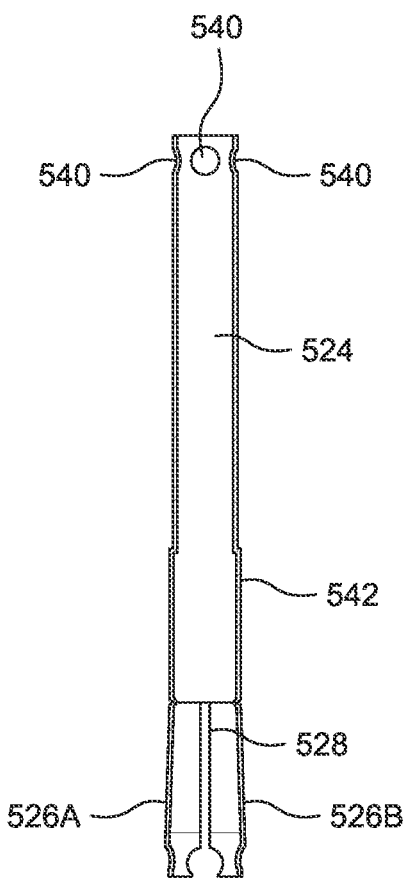
FIG. 32 is a cross-sectional view taken along lines 31A-31A in FIG. 31.

Referring to FIGS. 30-32, an illustrative embodiment of the inner member or tower 510 is shown. The tower 510 comprises a main body 516 having a first end 518 and a second, opposing end 520. The first end 518 includes an opening 522, exposing an interior 524. The interior 524 is hollow or partially hollow. At the second end 520, the tower 510 comprises a plurality of flexible members 526, illustrated herein as flexible blades. The flexible members 526 are preferably made of a flexible material or are attached or integrally formed from the main body 516 in a manner to allow the flexible members 526 to expand or move when a force is applied. When the force is removed, the flexible members 526 return to their original starting position or orientation. The flexible members 526, referred to individually as flexible members 526A, 526B, 526C, and 526D, are configured to engage with or secure to a portion (preferably the tulip) of the pedicle screw 14. Each flexible member 526A, 526B, 526C, and 526D is separated from adjacent flexible members 526A, 526B, 526C, and 526D by a gap or space 528, thereby allowing each flexible member 526A, 526B, 526C, and 526D to be movable independently of each other adjacent flexible member 526A, 526B, 526C, and 526D.

The tip 530 of each flexible member 526A, 526B, 526C, and 526D is configured to provide an engaging portion sufficient in size and shape to engage with or secure to a portion (preferably the tulip, and more preferably, to an outer surface protuberance) of the pedicle screw 14. The tip 530 comprises a generally flat or linear surface 532 surrounded by a pair of curved surfaces 534 and 536. The curved surfaces 534 and 536 preferably have a concave surface and, when aligned with a tip 530 associated with an adjacent flexible member 526A, 526B, 526C, or 526D, form a preexisting surgical hardware engagement member 538, illustrated herein as a partial or open circle. Since the tower 510 comprises four flexible members 526A, 526B, 526C, and 526D, four preexisting surgical hardware engagement members 538 are formed. Two of the four preexisting surgical hardware engagement members 538 engage or secure with the pedicle screw 14, and two of the four preexisting surgical hardware engagement members 538 engage, secure, or mount to the rod 22. The two, preexisting surgical hardware engagement members 538 that engage or secure with the pedicle screw are arranged or aligned in one plane. The two, preexisting surgical hardware engagement members 538 that engage or secure with the rod are arranged or aligned in a second plane; the second plane being different than the first plane. Preferably, the first plane is arranged or oriented at a 90-degree angle from the second plane. Such orientation allows the tower 510 to secure or engage with two different structures (pedicle screw and rod) positioned at two different orientations.

A plurality of openings 540 may be positioned at or near the first end 518 of the tower main body 516. The plurality of openings 540 are sized and shaped to accept extensions from a separate retractor system. As illustrated, the tower main body 516 comprises four openings 540. In this embodiment, the four openings 540 are positioned circumferentially around the tower main body 516. The tower main body 516 may also include external threading 542.

Figure 33:
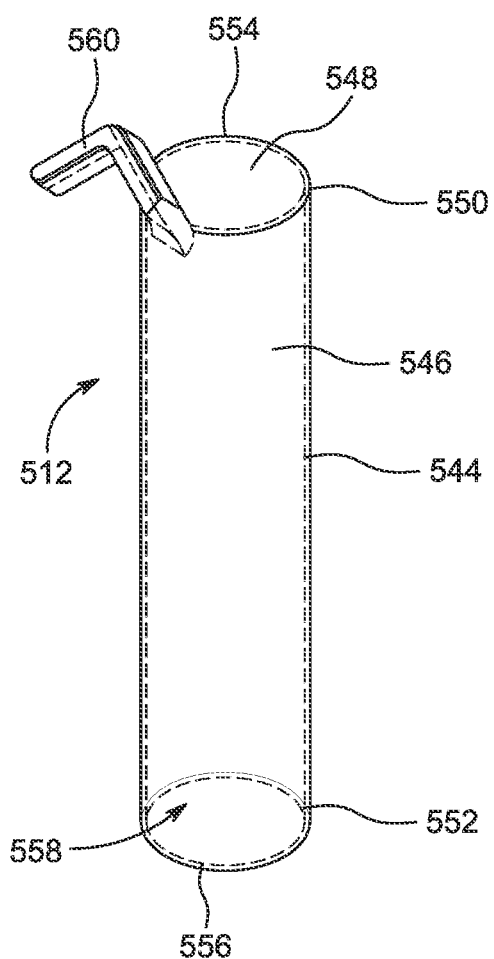
FIG. 33 is a perspective view of an illustrative embodiment of a dilator of the tower assembly.
Figure 34:
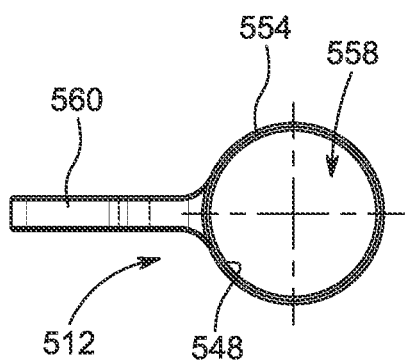
FIG. 34 is a top view of the dilator illustrated in FIG. 33.
Figure 35:
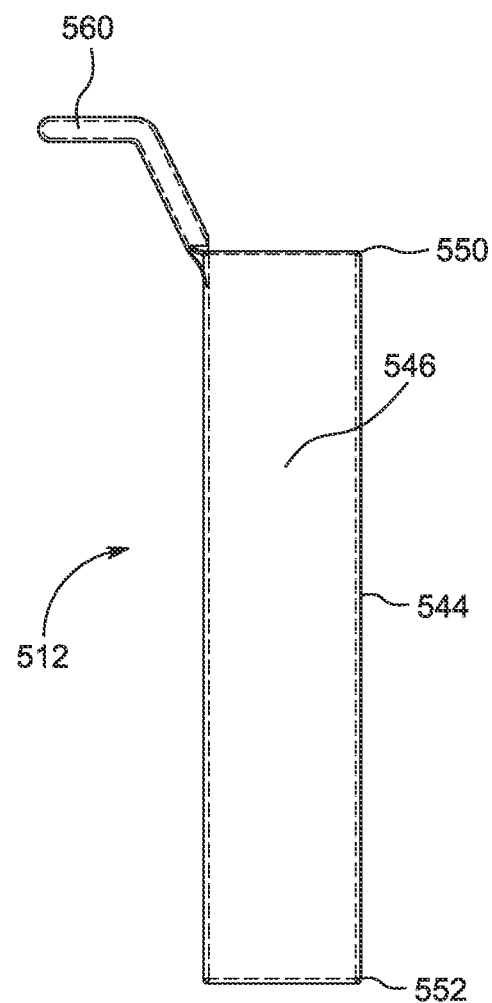
FIG. 35 is a side view of the dilator illustrated in FIG. 33.

Referring to FIGS. 33-35, an illustrative embodiment of the outer member or dilator 512 is shown. The outer member or dilator 512 comprises a main body 544, illustrated herein as an elongated, generally cylindrically shaped body having an outer surface 546 and an inner surface 548. The main body 544 has a first end 550 and a second, opposing end 552. The first end 550 has a first opening 554. The second end 552 has a second opening, 556. The internal portion 558 is hollow or partially hollow and of sufficient size and diameter to allow the inner component or tower 510 and the intermediate component or locking sleeve 514, individually or in combination, to fit and move within. At the first end 550, the outer member or dilator 512 may contain a handle 560. The handle 560 may be sized and shaped to provide a user a mechanism to move and place the outer component or dilator 512 where needed.

Figure 38:
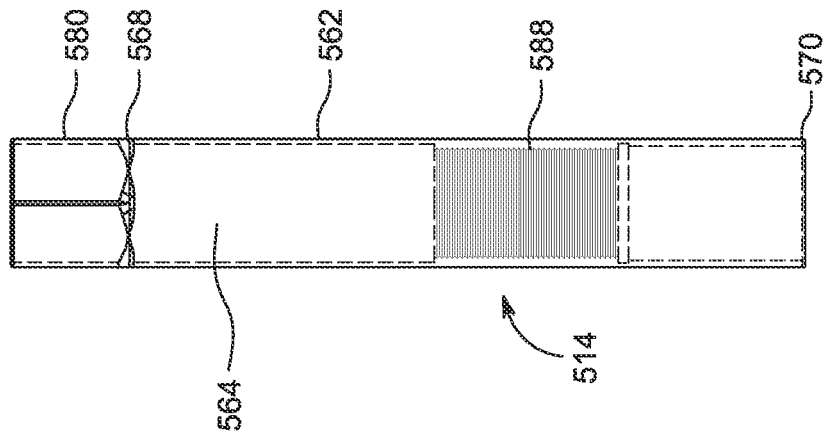
FIG. 38 is a side view of the locking sleeve illustrated in FIG. 36.
Figure 37:
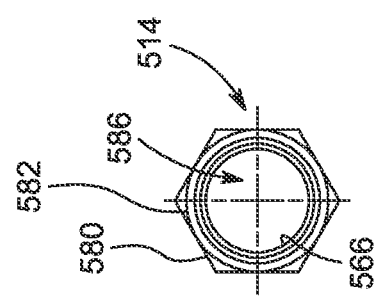
FIG. 37 is a top view of the locking sleeve illustrated in FIG. 36.
Figure 36:
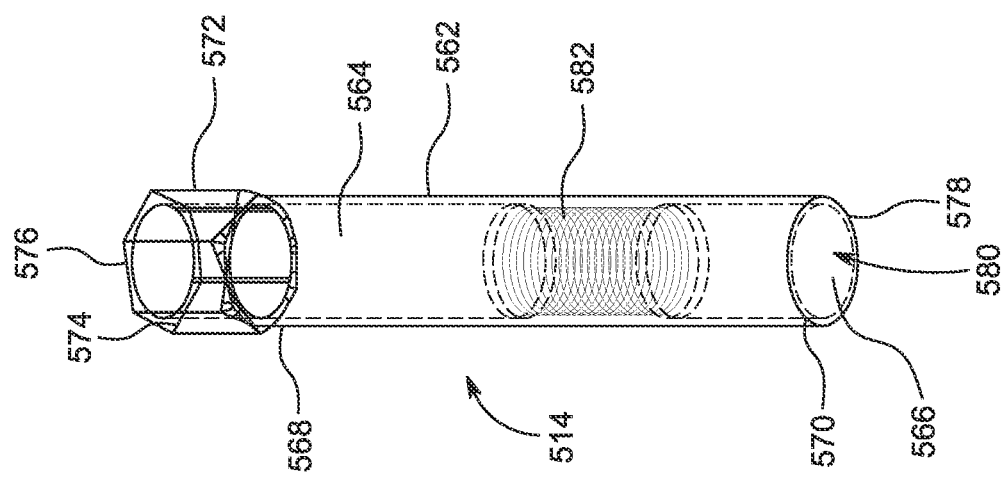
FIG. 36 is a perspective view of an illustrative embodiment of a locking sleeve of the tower assembly.
Figure 39A:
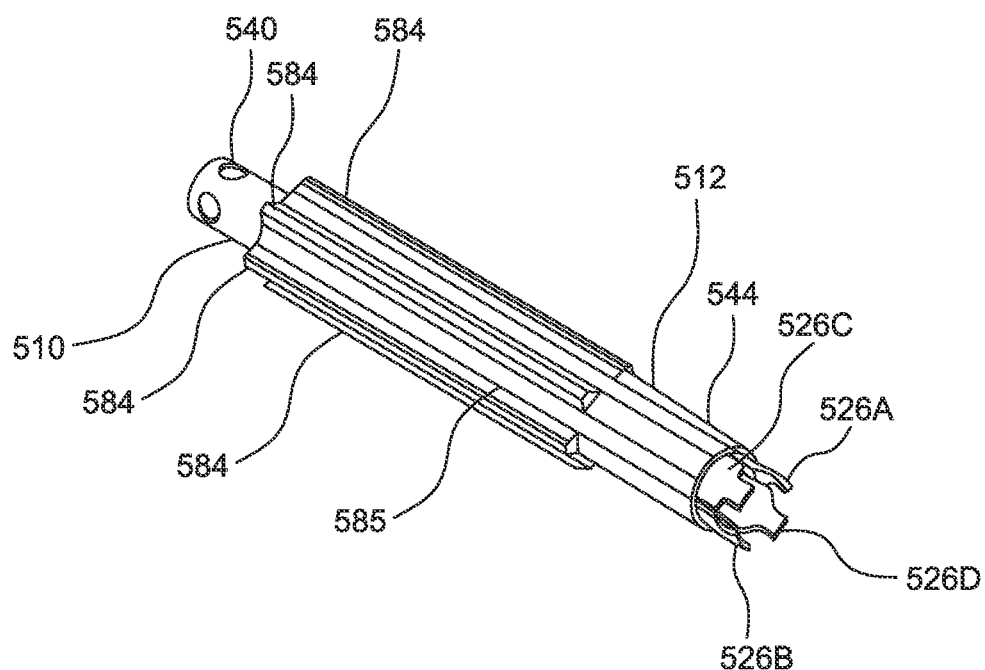
FIG. 39A is a perspective view of the tower assembly illustrated with an alternative embodiment of a dilator.
Figure 39B:
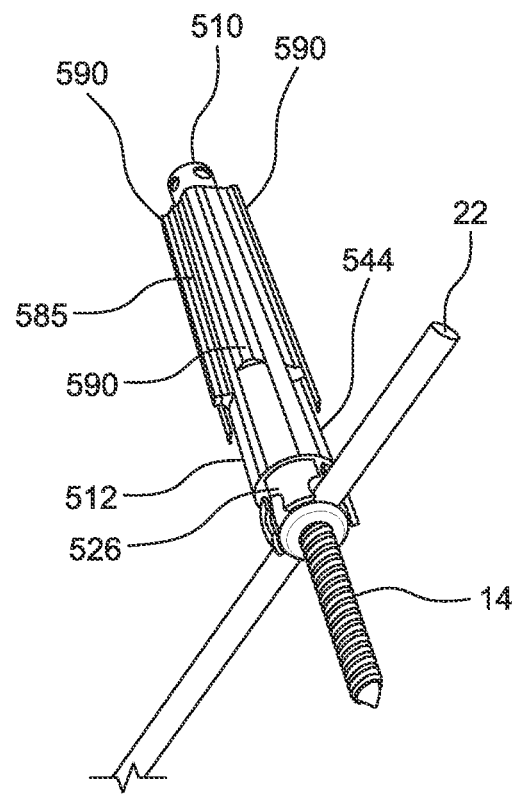
FIG. 39B illustrates the tower assembly illustrated in FIG. 39A secured to a pedicle screw.
Figure 40:
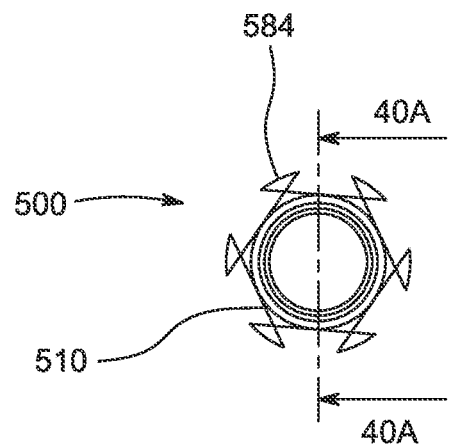
FIG. 40 is a top view of the tower assembly illustrated in FIG. 39A.
Figure 41:
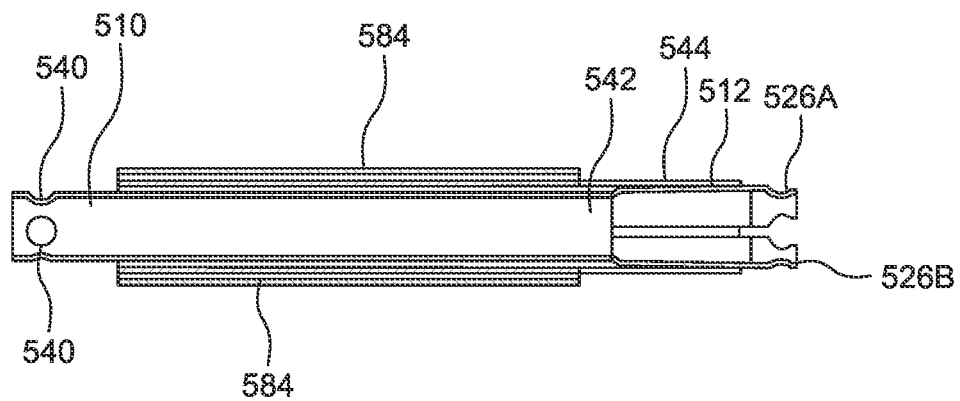
FIG. 41 is a cross-sectional view taken along lines 40A-40A in FIG. 40.

Referring to FIGS. 36-38, an illustrative embodiment of the intermediate member or locking sleeve 514 is shown. The intermediate member or locking sleeve 514 is configured to fit or slide over and secure or lock to the inner member or tower 512. The intermediate member or locking sleeve 514 comprises a main body 562, illustrated herein as an elongated, generally cylindrically shaped body having an outer surface 564 and an inner surface 566. The intermediate member or locking sleeve main body 562 comprises a first end 568 and a second, opposing end 570. The first end 568 comprises an insertion tool engaging member 572, illustrated herein as a hexagonal shaped cap or body 574 having an opening 576. The insertion tool engaging member 572 is shaped to fit and engage with an instrument insertion tool, allowing the user to loosen or tightened the engagement of the intermediate member or locking sleeve 514 with the inner member or tower 512. The second end 570 has an opening 578. An internal portion 580 is hollow or partially hollow and of sufficient size and diameter to allow the inner component or tower 510 to fit and move within. Internal threading 582 corresponds or is conjugate (male/female) with the tower external threading 542. In use, therefore, the intermediate member or locking sleeve 514 may be rotated (for example, via engagement with the insertion tool engaging member 572) in a clockwise/counterclockwise direction to be secured or unsecured to/from the inner member or tower 512.

Referring to FIGS. 39A-41, an embodiment of the outer member or dilator 512 having external, longitudinal blades or fins 584 is shown. In the embodiment illustrated, the outer member or dilator main body 544 comprises a plurality of external blades or fins 584 arranged circumferentially thereabout. The external blades or fins 584 may be sized to extend the entire length of the outer member or dilator main body 544 or less than the entire length of the outer member or dilator main body 562. The plurality of external blades or fins 584 define a groove(s) or channel(s) 585. The groove or channel 585 may have a curvilinear shape to mirror the shape of a curvilinear retractor blade and provide retractor functionality. While the figures illustrate multiple blades or fins 584 and grooves or channels 584, the dilator main body 544 may include external blades or fins 584 forming a single groove or channel 585 per side.

Figure 42:
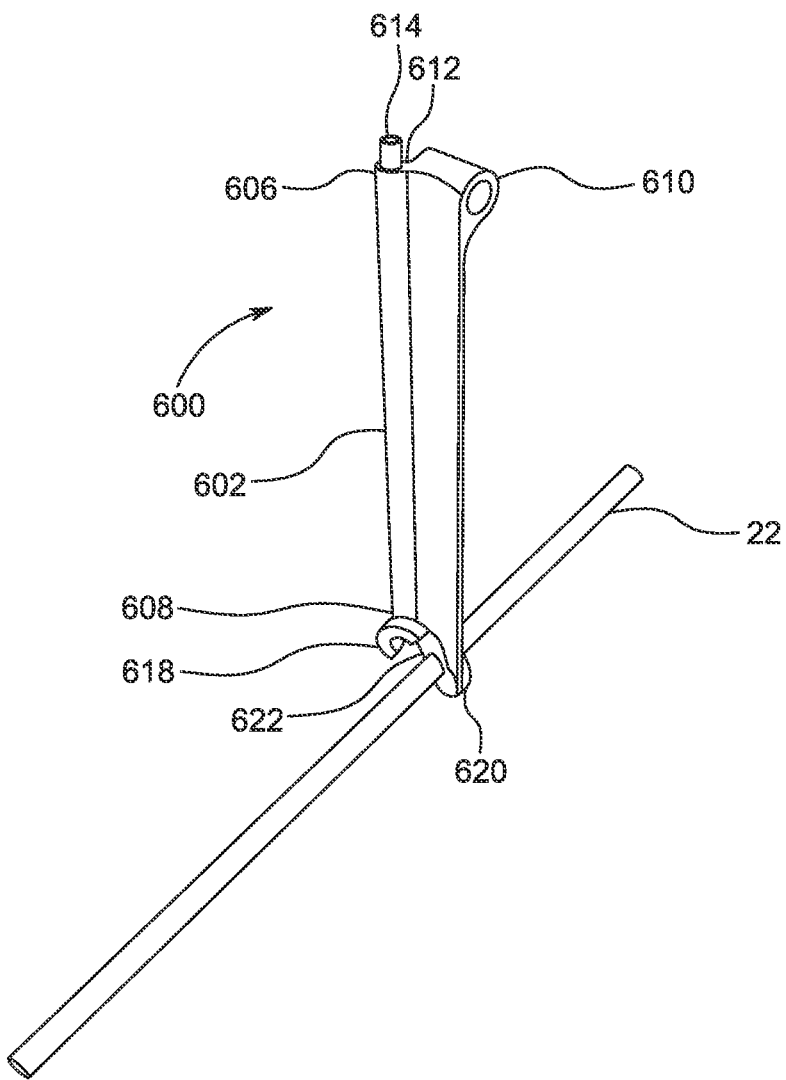
FIG. 42 is a perspective view of a retractor blade with a jaw like clamping mechanism.
Figure 43:
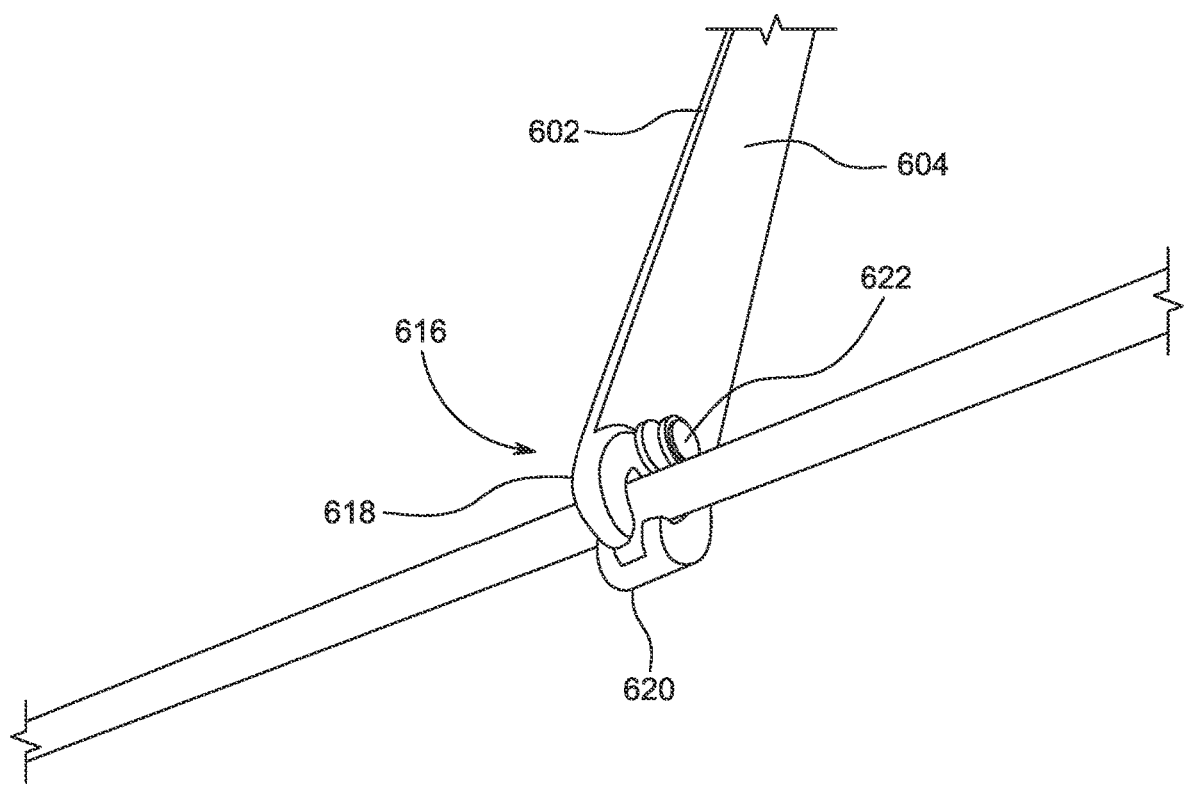
FIG. 43 is a bottom perspective view of the retractor blade illustrated in FIG. 42.
Figure 44:
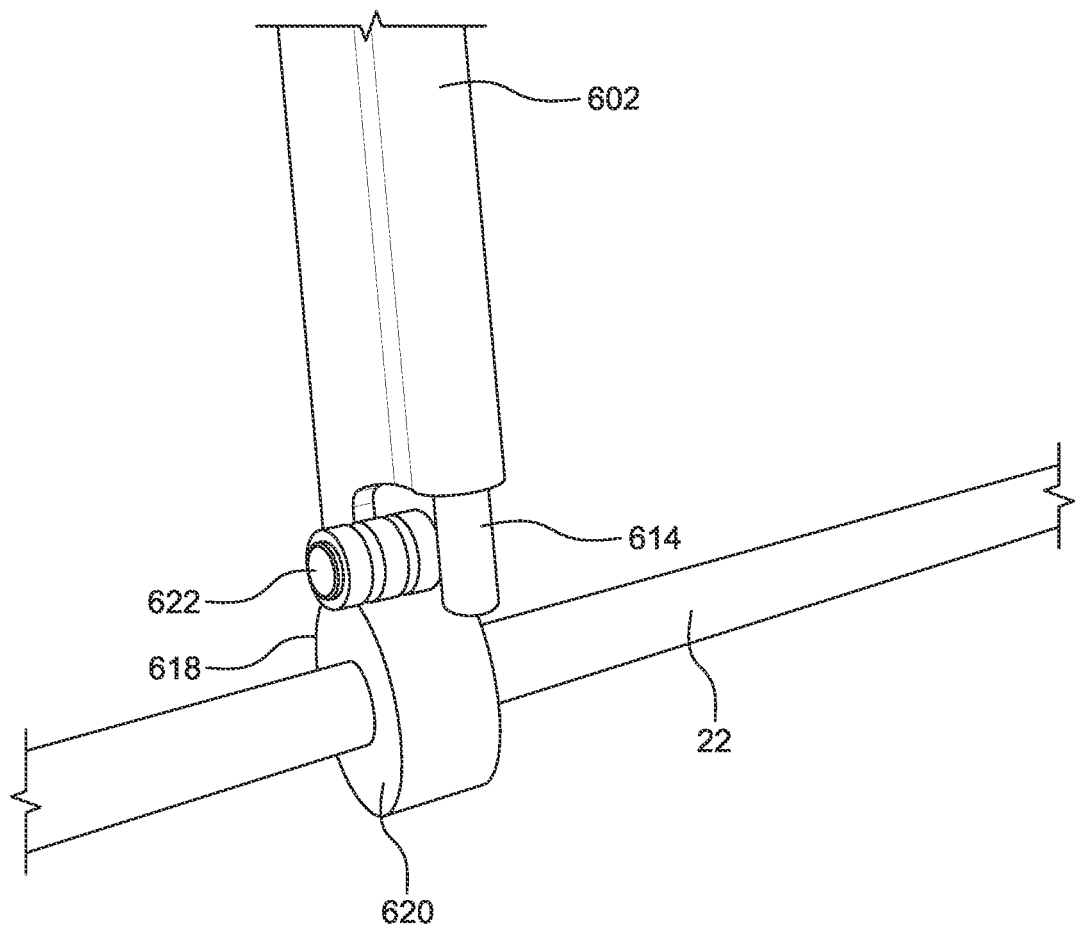
FIG. 44 is an alternative bottom perspective view of the retractor blade illustrated in FIG. 42.

Referring to FIGS. 42-44, an embodiment of a retractor blade with a jaw like clamping mechanism, referred to generally as a clamping retractor 600, is shown. The clamping retractor 600 comprises a main body 602, illustrated herein as an elongated body having an outer surface 604. The clamping retractor main body 602 comprises a first end 606 and a second, opposing end 608. The first end 606 comprises an opening 610 for securing to an independent retractor system or device and an opening 612 having a clamping actuator rod 614 inserted therein. The clamping retractor 600 is configured to secure to a structure, such as a rod 22 at the second end 608 via a clamping member 616. The clamping member 616 may include a first jaw member 618 having a C-shaped body and second jaw member 620 having a C-shaped body. The first jaw member 618 having a C-shaped body and the second jaw member 620 having a C-shaped body may be operationally held together via a pivot pint, such as pin 622. The clamping member 616 locks around the rod 22 as the first jaw member 618 and the second jaw member 620 are tightened to the rod 22. The clamping member 616 may be designed to allow the first jaw member 618 to move relative to a fixed second jaw member 620 (or vice versa), or both the first jaw member 618 and the second jaw member 620 are movable.

All patents and publications mentioned in this specification are indicative of the levels of those skilled in the art to which the invention pertains.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures, and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An apparatus configured to engage an anchoring point of an implanted bone screw system, the apparatus comprising:
    a first end separated from a second end by an elongated body;
    a set of apertures at the first end configured to engage structural elements of another retractor system; and
    a securing tip at the second end, wherein the securing tip selectively engages the anchoring point of the implanted bone screw system based on an amount of travel of a locking actuator along a length of the elongated body towards the second end, the locking actuator includes a main body with an inner surface and an outer surface, wherein the outer surface comprises a plurality of fins arranged to define one or more curvilinear channels sized to receive a retractor blade.

2. The apparatus of claim 1, wherein the locking actuator main body inner surface defines a bore sized to receive the elongated body.

3. The apparatus of claim 1, wherein the anchoring point includes a surgical rod or a tulip head sized to receive the surgical rod.

4. The apparatus of claim 1, wherein the securing tip is formed from a plurality of flexible members flexibly attached to the second end of the elongated body, and wherein the locking actuator traveling along the length of the elongated body causes the securing tip to selectively engage the anchoring point.

5. The apparatus of claim 4, wherein the securing tip is defined by terminal ends of the plurality of flexible members, and wherein the locking actuator traveling along the length of the elongated body towards the second end causes the plurality of flexible members to flex inwardly and causes the securing tip to enclose a tulip head within a volume of space defined by the securing tip or enclose a surgical rod within an opposing pair of partially circular apertures defined by the securing tip.

6. The apparatus of claim 5, wherein each of the plurality of flexible members includes an arcuate-shaped edge that defines the opposing pair of partially circular apertures.

7. A system comprising:
    an implanted bone screw system including at least one anchor point, the at least one anchor point including a connecting rod and a tulip head;
    a tower assembly coupled to the anchor point of the implanted bone screw system, the tower assembly comprising:
        a first end separated from a second end by an elongated body;
        a set of apertures at the first end configured to engage structural elements of another retractor system; and
        a securing tip at the second end, wherein the securing tip selectively engages the anchoring point of the implanted bone screw system based on an amount of travel of a locking actuator along a length of the elongated body towards the second end, the locking actuator includes a main body with an inner surface and an outer surface, wherein the outer surface comprises a plurality of fins arranged to define one or more curvilinear channels sized to receive a retractor blade.

8. A method of securing a tower assembly to an anchor point of an implanted bone screw system, the method comprising:
    aligning a securing tip of the tower assembly with the anchor point of the implanted bone screw system, wherein the tower assembly includes:
        a first end separated from a second end by an elongated body, wherein the securing tip is located at the second end, and
        a set of apertures at the first end configured to engage structural elements of another retractor system;
    actuating a locking actuator to cause the locking actuator to travel along a length of the elongated body towards the second end, wherein the securing tip selectively engages the anchor point of the implanted bone screw system based on an amount of travel of the locking actuator; and
    inserting a retractor blade into a curvilinear channel of the locking actuator, wherein the curvilinear channel is defined by a plurality of fins disposed on an outer surface of the locking actuator.

* * * * *